(12) United States Patent
Gibbs

(10) Patent No.: US 7,713,306 B2
(45) Date of Patent: *May 11, 2010

(54) METHOD AND APPARATUS FOR ACETABULAR RECONSTRUCTION

(75) Inventor: Phillip M Gibbs, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1285 days.

This patent is subject to a terminal disclaimer.

(21) Appl. No.: 10/700,292

(22) Filed: Nov. 3, 2003

(65) Prior Publication Data

US 2005/0021148 A1    Jan. 27, 2005

Related U.S. Application Data

(63) Continuation-in-part of application No. 10/201,485, filed on Jul. 23, 2002, now Pat. No. 7,291,177, which is a continuation-in-part of application No. 09/792,174, filed on Feb. 23, 2001, now Pat. No. 6,458,161.

(51) Int. Cl.
*A61F 2/32* (2006.01)

(52) U.S. Cl. .................................... 623/22.25
(58) Field of Classification Search .............. 623/16.11, 623/18.11, 22.11–22.39
See application file for complete search history.

(56) References Cited

U.S. PATENT DOCUMENTS

| | | | |
|---|---|---|---|
| 3,840,904 A | 10/1974 | Tronzo | |
| 4,743,262 A | 5/1988 | Tronzo | |
| 4,795,469 A | 1/1989 | Oh et al. | |
| 4,892,549 A * | 1/1990 | Figgie et al. | 623/22.23 |
| 4,923,473 A | 5/1990 | Griss et al. | |
| 4,936,856 A | 6/1990 | Keller | |
| 4,978,356 A | 12/1990 | Noiles | |
| 5,002,577 A * | 3/1991 | Bolesky et al. | 623/22.25 |

(Continued)

FOREIGN PATENT DOCUMENTS

DE    32 05 526    9/1983

(Continued)

OTHER PUBLICATIONS

Michael S. Bradford, M.D. and Wayne G. Paprosky, M.D., F.A.C.S., Total Acetabular Transplant Allograft Reconstruction of the Severely Deficient Acetabulum, Sunrise Hospital and Medical Center, Las Vegas, NV and Rush-Presbyterian-St. Lukes Medical Center, Chicago, IL, 1995 by W.B. Saunders Company, pp. 1-15.

(Continued)

*Primary Examiner*—Anu Ramana
(74) *Attorney, Agent, or Firm*—Harness, Dickey

(57) ABSTRACT

A trial system for an acetabular prosthesis is described. The acetabular prosthesis is generally for implantation in an acetabulum and surrounding pelvis. The acetabular prosthesis includes an acetabular cup having a substantially concave inner surface and a substantially convex outer surface. The described acetabular prosthesis is especially useful in revision hip implant procedures where significant bone tissue loss has occurred either in or around the acetabulum and/or the pelvis. A collection of trial shells are provided to trial a range of motion of the hip joint before implanting a prosthetic shell into the acetabular prosthesis.

31 Claims, 15 Drawing Sheets

U.S. PATENT DOCUMENTS

| | | | |
|---|---|---|---|
| 5,156,626 A | 10/1992 | Brocerick et al. | |
| 5,176,711 A | 1/1993 | Grimes | |
| 5,211,665 A | 5/1993 | Ku | |
| 5,314,490 A | 5/1994 | Wagner et al. | |
| 5,326,367 A | 7/1994 | Robioneck | |
| 5,326,368 A | 7/1994 | Collazo | |
| 5,370,704 A | 12/1994 | DeCarlo | |
| 5,507,824 A * | 4/1996 | Lennox | 623/22.25 |
| 5,658,348 A * | 8/1997 | Rohr, Jr. | 623/22.29 |
| 5,702,477 A | 12/1997 | Capello et al. | |
| 5,871,548 A | 2/1999 | Sanders et al. | |
| 5,879,401 A | 3/1999 | Besemer et al. | |
| 5,916,268 A | 6/1999 | Schollner et al. | |
| 5,931,870 A | 8/1999 | Cuckler et al. | |
| 6,162,257 A | 12/2000 | Gustilo et al. | |
| 6,273,891 B1 | 8/2001 | Masini | |
| 6,306,173 B1 | 10/2001 | Masini | |
| 6,340,370 B1 | 1/2002 | Willert et al. | |
| 6,416,553 B1 | 7/2002 | White et al. | |
| 6,458,161 B1 | 10/2002 | Gibbs et al. | |
| 6,527,809 B1 * | 3/2003 | Doursounian et al. | 623/22.28 |
| 6,682,566 B2 * | 1/2004 | Draenert | 623/22.24 |
| 6,926,740 B2 * | 8/2005 | Lewis et al. | 623/22.28 |
| 2003/0171818 A1 | 9/2003 | Lewallen | |
| 2004/0054421 A1 | 3/2004 | McLean | |

FOREIGN PATENT DOCUMENTS

| | | |
|---|---|---|
| DE | 41 33 433 C1 | 5/1993 |
| EP | 0 551 794 A1 | 7/1993 |
| EP | 0 612 509 | 8/1994 |
| EP | 0 807 426 | 11/1997 |
| EP | 1 082 949 | 3/2001 |
| EP | 1 236 450 | 9/2002 |
| EP | 1 384 456 | 1/2004 |
| FR | 2 148 322 | 3/1973 |
| FR | 2775586 | 9/1999 |
| GB | 2 001 247 | 1/1979 |
| WO | WO01/70141 | 9/2001 |

OTHER PUBLICATIONS

Overview of Anatomy, Clinically Oriented Anatomy, pp. 1-6.

Michael S. Bradford, M.D. and Wayne G. Paprosky, M.D., F.A.C.S., Total Acetabular Transplant Allograft Reconstruction of the Severely Deficient Acetabulum, Sunrise Hospital and Medical Center, Las Vegas, NV and Rush-Presbyterian-St. Lukes Medical Center, Chicago, Il, 1995 by W.B. Saunders Company, pp. 1-15.

Overview of Anatomy, Clinically Oriented Anatomy, pp. 1-16.

* cited by examiner

METHOD AND APPARATUS FOR ACETABULAR RECONSTRUCTION

CROSS-REFERENCE TO RELATED APPLICATIONS

This application is a continuation-in-part of U.S. Ser. No. 10/201,485, filed Jul. 23, 2002, which is a continuation-in-part of U.S. Ser. No. 09/792,174, filed Feb. 23, 2001, the entire contents of which are hereby expressly incorporated by reference into the present application.

TECHNICAL FIELD

This invention relates generally to a method and apparatus for use in orthopedic surgery and, more particularly, to a method and apparatus for trialing a modular acetabular prosthesis having various modular attachment components for use during an orthopedic surgical procedure.

BACKGROUND

A natural hip joint may undergo degenerative changes due to a variety of etiologies. When these degenerative changes become so far advanced and irreversible, it may ultimately become necessary to replace a natural hip joint with a prosthetic hip. When implantation of such a hip joint prosthesis becomes necessary, the head of the femur, the acetabular, or both may need to be replaced. The head of the natural femur is first resected and a cavity is created within the intramedullary canal of the host femur for accepting the hip prosthesis. The hip prosthesis may be inserted and supported within the host femur by cementing the hip prosthesis within the host femur. Alternatively, the hip prosthesis may be impacted into the host femur so that it is snugly fit and supported by the host femur. If the acetabulum also needs repair, all remnants of articular cartilage are generally removed from the acetabulum and an acetabular prosthesis which will accommodate the head or ball of the hip prosthesis is affixed to the acetabulum. The acetabular prosthesis is affixed to the acetabulum by means of cement, screws or other appropriate fixation means.

Due to any number of reasons, however, a small portion of patients that undergo such orthopedic surgical procedures may require subsequent revision surgery to replace the prosthetic device with a new prosthetic device generally referred to as a revision prosthesis. One example of such a device is generally known as a protrusio cage.

In this regard, a revision acetabular prosthesis will generally include additional mounting points, such as integral extension members or hooks that provide additional stability for the revision acetabular prosthesis. These additional mounting points are generally required due to additional bone loss or defects exhibited at the acetabulum, such as collar/rim defects or pelvic discontinuity defects.

Various types of revision acetabular prostheses are currently available and different surgeons prefer different types of revision acetabular prostheses. Some surgeons prefer to use what is known as an ilium flange that is formed integral with the acetabular prosthesis and enables further securement of the acetabular prosthesis in the ilium region of the pelvis. Other surgeons prefer to use what is known as an obturator hook that is able to provide inferior fixation of the acetabular prosthesis by engaging the obturator foramen which is a large aperture adjacent the acetabulum. Because of this, a hospital must maintain a large inventory of different revision acetabular cups to meet the various surgeons preferences. Moreover, the surgeon generally requires several revision acetabular cups available during surgery to account for any type of condition that may arise during the surgical procedure. This increased inventory of prosthetic devices increases the overall hospital costs and inventory control. Furthermore, by requiring the multiple revision acetabular cups to be available during the surgical procedure, multiple prosthetic devices must be sterilized prior to the surgical procedure, thereby increasing the surgical time, cost and complexity.

Regardless of the reason for the revision implant, or the use of the protrusio cage acetabular implant, the use of such a system requires first affixing the cage to the bone portion remaining in the patient and then affixing an acetabular shell or liner relative to the cage. The cage assists in reinforcing the bone structure of the patient, while the shell provides the bearing surface for the head of the femur or the ball of the implant.

The shell may be made out of any appropriate material, but is generally made of a ultra high molecular weight polyethylene. The shell is generally affixed into the protrusio cage with bone cement to complete the acetabular reconstruction. Because of this two piece system and type of attachment, however, it is often difficult for the surgeon to precisely implant the shell due to the relatively unconstrained possibilities of placing the shell in the protrusio cage. Moreover, there is not a way of fixing the shell within the protrusio cage before implanting the shell into the cage to test a range of motion of the hip joint after implantation into the shell.

Therefore, it is desired to provide a protrusio cage and shell implant that will allow a trialing of the hip joint through a range of motion before affixing the shell to the protrusio cage. Moreover, it is desired to provide a protrusio cage, which will allow for a trialing shell to be selectively and removably affixed to the implanted protrusio cage so that a hip joint may be trialed through a range of motion before affixing the implant shell. Finally, it is also desired to provide a collection of trial shells each having one degree of freedom and mountable in a distal orientation with respect to the protrusion cage, that may be placed in the resected acetabulum to determine a proper orientation of the protrusio cage before implanting the final cage.

SUMMARY OF THE DISCLOSURE

A system to provide a determination of an alignment of a prosthetic bearing in an acetabular prosthesis includes a trial shell having an attachment device thereon. An attachment member is moveable between a locating position and a fastened position to selectively and operably interconnect the trial shell to the acetabular prosthesis at the attachment device. The trial shell is moveable in one degree of freedom around an axis defined by the attachment member in the locating position and substantially immobile relative to the acetabular prosthesis in the fastened position.

In other features an acetabular cup generally defines a portion of a hollow sphere and includes a bore therein. The attachment member engages the bore in the locating position and the fastened position. The attachment member includes an attachment end engaged with the bore and a central portion extending between the attachment device. An engagement end manipulates the attachment member between the locating and the fastened position.

The acetabular cup includes an outer rim defining an acetabular cup plane. The trial shell includes an outer rim defining a trial shell plane. The location of the attachment device determines a predetermined angle the trial plane is oriented from the acetabular cup plane.

A method of implanting an acetabular prosthesis in an acetabulum and providing a liner in the acetabular prosthesis in a selected orientation includes implanting the acetabular prosthesis. A first trial shell is disposed in the acetabular prosthesis, the first shell having an outer dimension defining a first plane and extending at a first angle from the acetabular prosthesis. The first trial shell, having one degree of freedom, is oriented in a first orientation. The first trial shell is fixed in the first orientation. A femur is moved through a range of motion relative to the first trial shell.

According to other features, the first trial shell is removed. A second trial shell is disposed in the acetabular prosthesis. The second trial shell has an outer dimension defining a second plane and extends at a second angle from the acetabular prosthesis. The second angle is distinct from the first angle. The second trial shell, having one degree of freedom, is oriented in a second orientation. The second trial shell is fixed in the second orientation. The femur is moved through a range of motion relative to the second trial shell.

A more complete appreciation of the present invention and its scope can be obtained from the following detailed description of the invention, the drawings and the appended claims.

BRIEF DESCRIPTION OF THE DRAWINGS

The present invention will become more fully understood from the detailed description and the accompanying drawings, wherein:

FIG. 17A is a perspective view of a protrusio cage implanted in an acetabulum and a trialing cup in a first position;

FIG. 17B is a protrusio cage implanted in an acetabulum and the trialing cup in a second position different from that illustrated in FIG. 17a;

The same reference numerals refer to the same parts throughout the various FIGS.

DETAILED DESCRIPTION OF THE EMBODIMENTS

Figure 1:
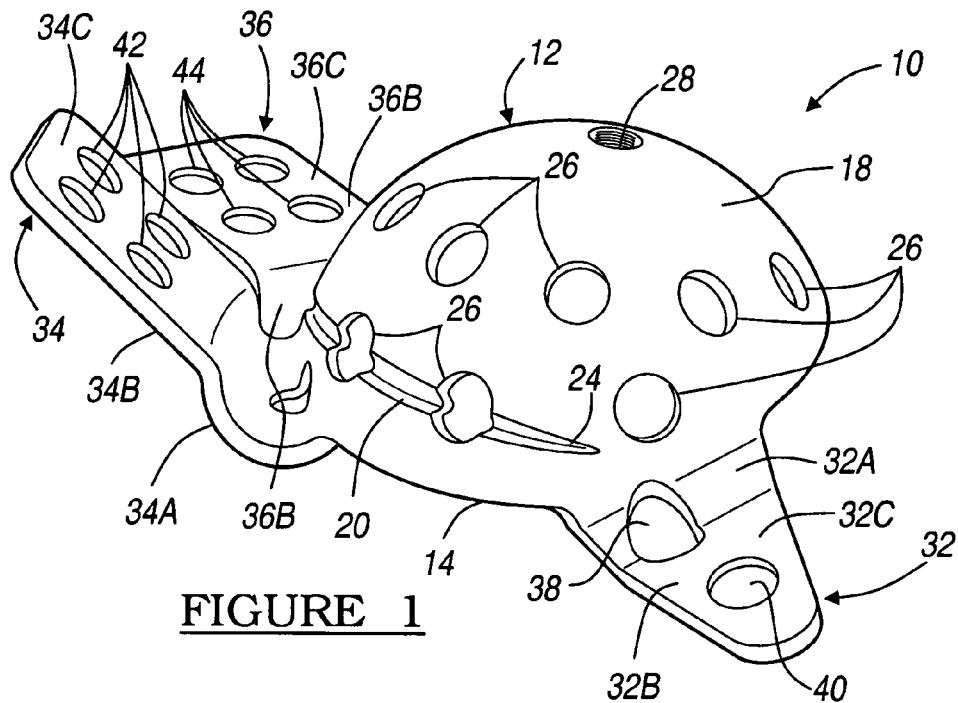
FIG. 1 is a rear perspective view of an acetabular prosthesis, in accordance with one embodiment of the present invention.
Figure 2:
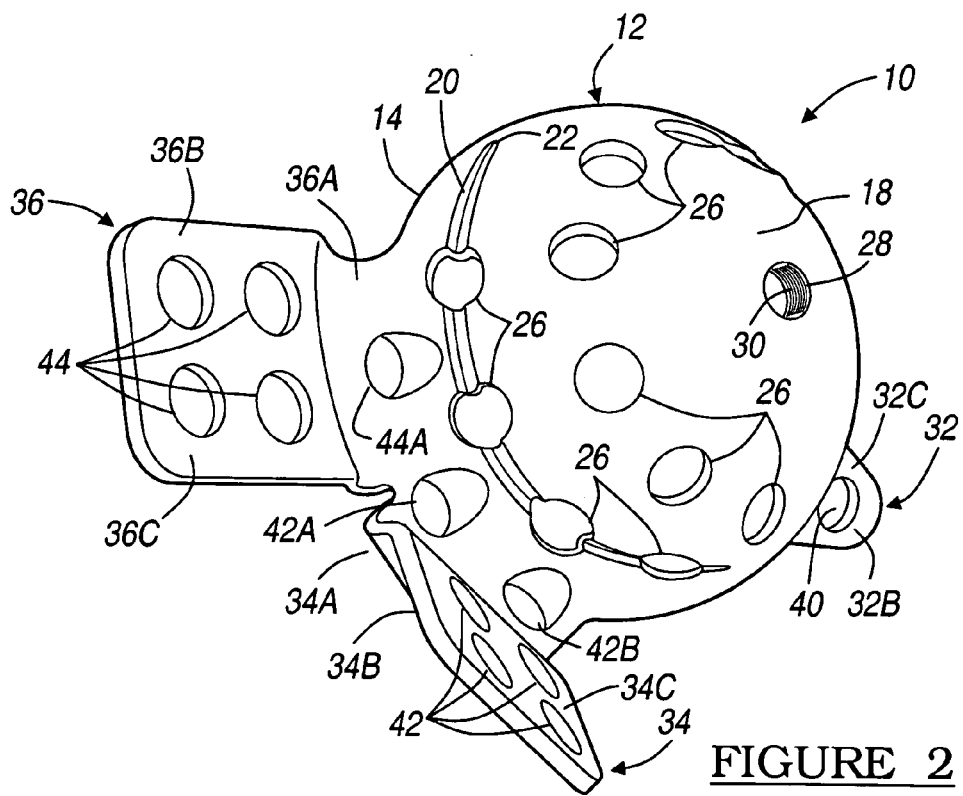
FIG. 2 is another rear perspective view of an acetabular prosthesis, in accordance with one embodiment of the present invention.
Figure 3:
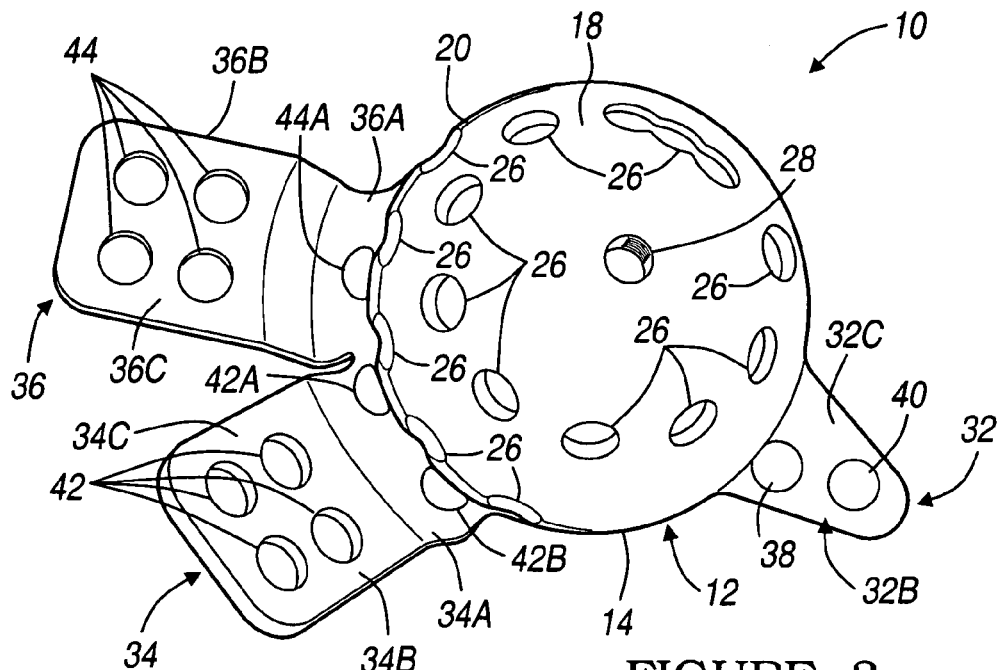
FIG. 3 is a rear elevational view of an acetabular prosthesis, in accordance with one embodiment of the present invention.
Figure 4:
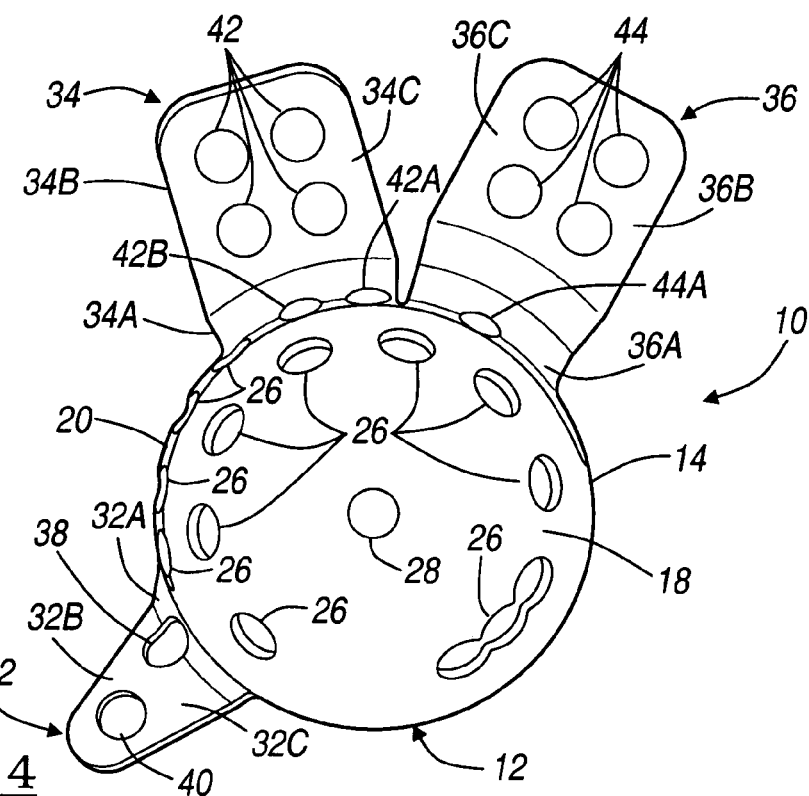
FIG. 4 is a rear plan view of an acetabular prosthesis, in accordance with one embodiment of the present invention.
Figure 5:
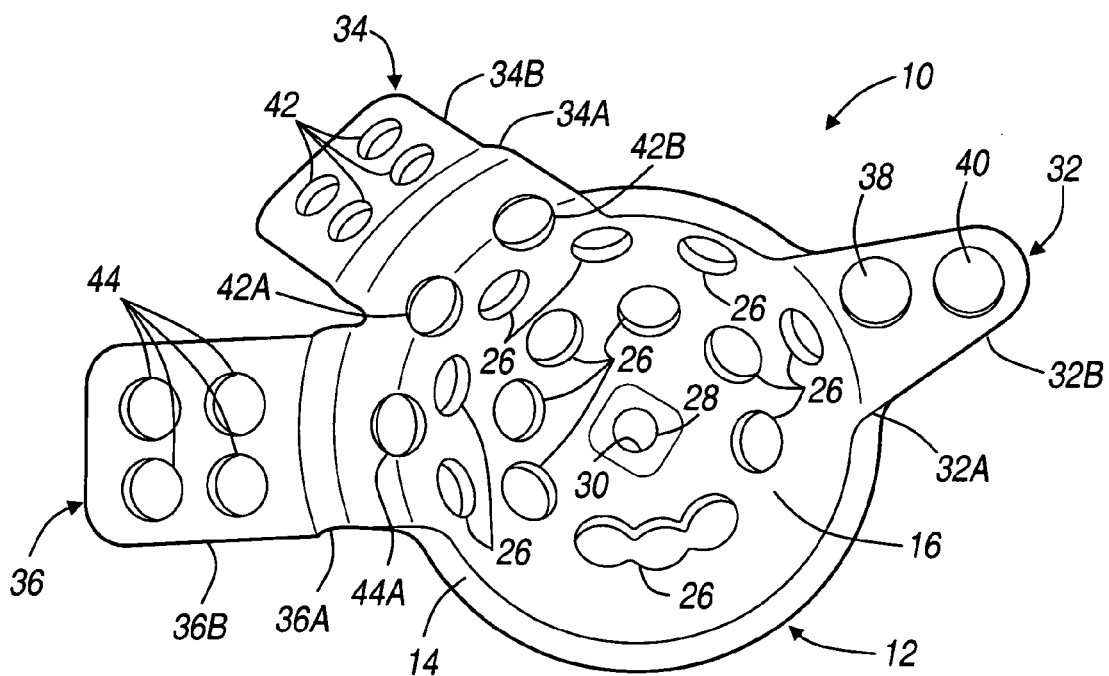
FIG. 5 is a front plan view of an acetabular prosthesis, in accordance with one embodiment of the present invention.
Figure 6:
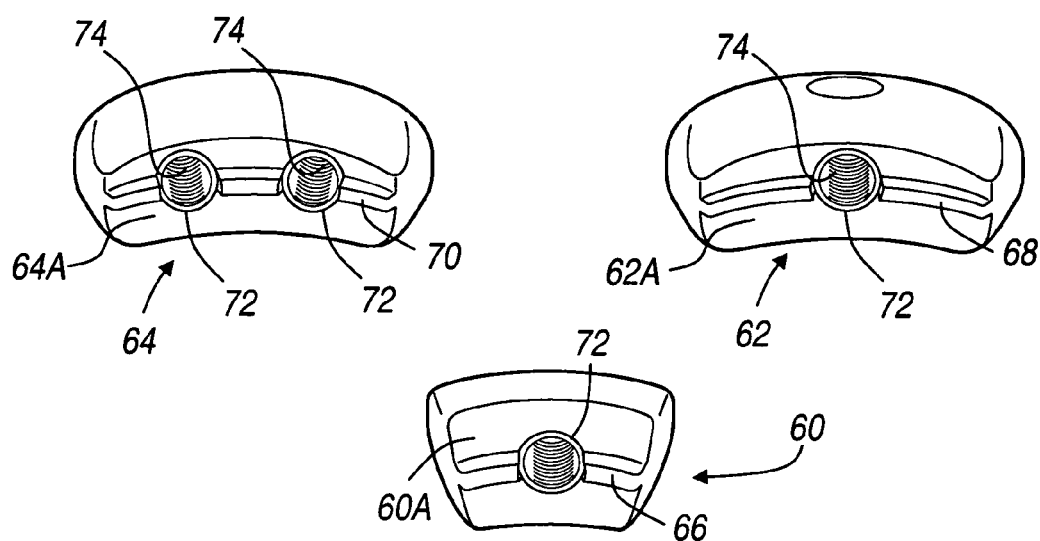
FIG. 6 is a side perspective view of several acetabular spacer members for an acetabular prosthesis, in accordance with one embodiment of the present invention.
Figure 7:
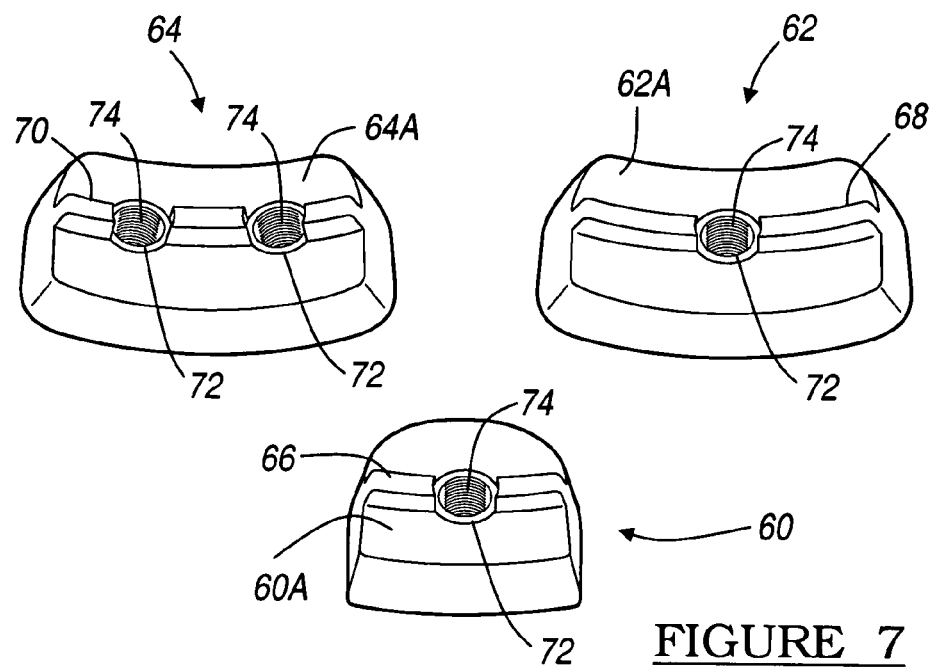
FIG. 7 is a bottom plan view of several acetabular spacer members for an acetabular prosthesis, in accordance with one embodiment of the present invention.
Figure 8:
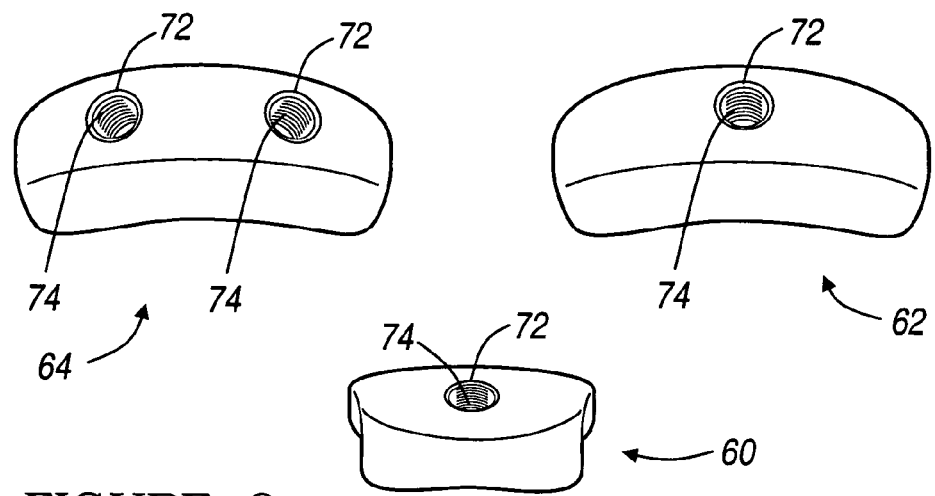
FIG. 8 is a top perspective view of several acetabular spacer members for an acetabular prosthesis, in accordance with one embodiment of the present invention.
Figure 9:
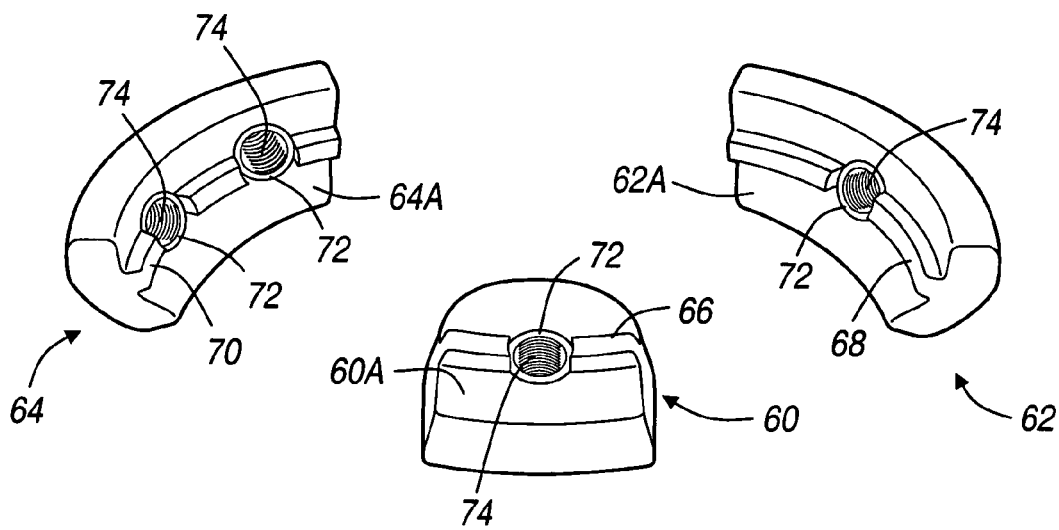
FIG. 9 is a bottom perspective view of several acetabular spacer members for an acetabular prosthesis, in accordance with one embodiment of the present invention.

The following description of the embodiments concerning a method and apparatus for providing a modular acetabular prosthesis for use in orthopedic surgical procedures, and trials therefore, are merely exemplary in nature and are not intended to limit the invention or its application or uses. Moreover, while the present invention is described in detail below with reference to performing a revision type implantation procedure, it will be appreciated by those skilled in the art, that the present invention is clearly not limited to only revision type orthopedic surgical procedures and may be used with various other orthopedic surgical procedures as well.

Referring to FIGS. 1-5, an acetabular prosthesis 10, according to a general embodiment, is shown. The acetabular prosthesis 10 includes a modified hemispherical acetabular cup 12. The acetabular cup 12 is said to be "hemispherical" in that it is not a perfect hemisphere; but rather, it includes an arcuate portion 14 extending along the periphery thereof without extending beyond the hemisphere of the acetabular cup 12.

The acetabular cup 12 is preferably constructed from any suitable biocompatible material, such as titanium, stainless steel, titanium alloy, cobalt-chrome-molybdenum alloy, and the like.

It should be noted that the acetabular cup 12 would normally also be associated with other components, such as a congruent shell or bearing liner (not shown) retained within the acetabular cup 12, via bone cement or a ring lock (not shown), which are not depicted for purposes of clarity.

The acetabular cup 12 preferably includes a substantially concave inner surface 16 and a substantially convex outer surface 18, wherein the outer surface 18 is operable to be received in the acetabulum. The inner surface 16 may be either roughened or smooth, whereas the outer surface 18 may be smooth or roughened with a grit blast or a porous surface layer (not shown) to facilitate bone tissue in-growth.

An area defining an optional receptacle or groove 20 is located in at least a portion of the outer surface 18 of the acetabular cup 12. The groove 20 may include tapered end portions 22, 24. The groove 20 is located in proximity to a peripheral surface of the acetabular cup 12, and generally in the superior and posterior region of the acetabular cup 12. The exact purpose of the groove 20 will be explained later in detail.

The acetabular cup 12 may include at least one, and generally, a plurality of throughbores 26 located therein. It should be noted that the groove 20 is bisected by at least one of the throughbores 26. The throughbores 26 provide a number of functions, such as enabling fastening members (not shown) to pass through the acetabular cup 12. Additionally, the throughbores 26 provide for the infiltration of bone cement to improve adhesion, as well as providing for new bone tissue in-growth. At least one of the throughbores 28 includes a threaded surface 30 thereon for receiving an insertion instrument (not shown) for properly aligning the acetabular prosthesis 10 within the acetabulum. Throughbore 28 also includes a recessed area 28A which permits the insertion instrument (not shown) to securely engage the acetabular cup 12 and permits controlled rotation of same. It will be noted that any graft material and/or bone cement should preferably be placed into the acetabulum before securing the acetabular cup 12 thereto.

A more specific description of the typical installation of an acetabular prosthesis can be found in U.S. Pat. Nos. 5,314, 490; 5,326,367; 5,326,368; 5,702,477; 5,871,548; 5,931,870; and 6,162,257, the entire specifications of which are incorporated herein by reference.

The acetabular cup 12 preferably includes at least one, and more preferably, three substantially rigid attachment or extension members 32, 34, and 36 integrally formed with the acetabular cup 12 for fastening the acetabular prosthesis 10 to at least a portion of one or more surfaces of the pelvis (not shown), such as the ilium and/or the ischium. Preferably, attachment member 32 is used for attachment to the ischium, whereas attachment members 34 and 36 are used for attachment to various surfaces of the ilium (e.g., anterior and posterior).

Attachment member 32 is shown as being substantially triangularly shaped; however, it is envisioned that the shape may be altered to other configurations. It will be noted that attachment member 32 has two distinct portions, i.e., a first substantially curved portion 32A originating from, and contiguous with, the inner surface 16 of the acetabular cup 12, and a second substantially planar portion 32B extending out from, and angling away from, the first portion 32A. The curvature profile may be modified to meet any anatomical requirements.

Attachment member 32 preferably includes at least one, and more preferably, a plurality of throughbores located therein. In this view, a throughbore 38 is provided in the curved portion 32A and another throughbore 40 is provided in the planar portion 32B. The throughbores 38, 40 provide a number of functions, such as enabling fastening members such as a surgical screw (not shown) to pass therethrough in order to allow the fastening member 32 to be secured to the ischium.

Attachment member 34 is shown as being substantially rectangularly shaped; however, it is envisioned that the shape may be altered to other configurations. It will be noted that attachment member 34 has two distinct portions, i.e., a first substantially curved portion 34A originating from, and contiguous with, the inner surface 16 of the acetabular cup 12, and a second substantially planar portion 34B extending out from, and angling away from, the first portion 34A. The curvature profile may be modified to meet any anatomical requirements.

Attachment member 34 preferably includes at least one, and more preferably, a plurality of throughbores 42 located therein. In this view, additional throughbores 42A and 42B are provided in the curved portion 34A. The throughbores 42, 42A, and 42B provide a number of functions, such as enabling fastening members such as a surgical screw (not shown) to pass therethrough in order to allow the fastening member 34 to be secured to at least a portion of a surface of the ilium.

Attachment member 36 is also shown as being substantially rectangularly shaped; however, it is envisioned that the shape may be altered to other configurations. It will be noted that attachment member 36 also has two distinct portions, i.e., a first substantially curved portion 36A originating from, and contiguous with, the inner surface 16 of the acetabular cup 12, and a second substantially planar portion 36B extending out from, and angling away from, the first portion 36A. Again, the curvature profile may be modified to meet any anatomical requirements.

Attachment member 36 preferably includes at least one, and more preferably, a plurality of throughbores 44 located therein. In this view, an additional throughbore 44A is provided in the curved portion 36A. The throughbores 44 and 44A provide a number of functions, such as enabling fastening members such as a surgical screw (not shown) to pass therethrough in order to allow the fastening member 36 to be secured to at least another portion of a surface of the ilium spaced away from attachment member 34.

The installation of the acetabular prosthesis 10 would be accomplished in any number of ways, as are currently known in the art. The surgeon would surgically prepare the acetabulum and surrounding pelvic area to receive the acetabular prosthesis 10. This preparation would typically include removing any debris (e.g., bone fragments, bone cement) from the acetabulum. The surgeon would then install an allograft, if necessary, and install bone cement, if necessary, into the acetabulum. The acetabular cup 12 would then be received into, and anatomically aligned with, the acetabulum. At least one fastening member, such as a surgical screw, would then be placed through one of the throughbores 26 and into the interior of acetabulum, thus securing the acetabular cup 12 to the acetabulum. The attachment members 32, 34, and 36 would then be secured to the ischium and ilium, respectively, with fastening members, such as surgical screws.

However, if the acetabulum and/or the surrounding pelvic structures have any significant defects present, the loading will be borne primarily by the allograft and/or bone cement material, as previously described. Therefore, it is desirable to have the surfaces of the acetabular prosthesis 10 actually abut against the respective surfaces of the acetabulum and/or the surrounding pelvic structures, as opposed to using allografts and bone cement to fill the gap therebetween. Because the acetabular prosthesis 10 is constructed of metallic material, it is much stronger than allografts and bone cement, and therefore is much more able to withstand the loads and forces associated with standing, walking, and running activities.

Therefore, the present invention may employ at least one augment or spacer member to compensate for the fact that the acetabulum and/or the surrounding pelvic structures may have defects therein which prevent the outer surface 18 of the acetabular cup 12 from contacting the surface of the acetabulum, and/or the outer surfaces 32C, 34C, and 36C, respectively, from contacting the respective surfaces of the pelvis, i.e., the ischium and the ilium.

The spacer members are preferably constructed from any suitable biocompatible material, such as titanium, stainless steel, titanium alloy, cobalt-chrome-molybdenum alloy, etc. and is preferably made of the titanium alloy Ti-6Al-4V.

Referring to FIGS. 6-9, several different types of acetabular spacer members 60, 62, and 64 for use with the outer surface 18 of the acetabular cup 12, according to the general teachings of the present invention, are shown. It should be noted that only one spacer member would generally be used at a time in practice; however, multiple spacer members may be used in some instances. For example, if there is a relatively small defect in the superior region of the acetabulum, acetabular spacer member 60 can be employed. If there is a larger defect, either acetabular spacer member 62 or 64 may be used. It is envisioned that either smaller and/or larger acetabular spacer members may also be employed with the present acetabular prosthesis.

The acetabular spacer members 60, 62, and 64 may be substantially curved so that the lower surfaces 60A, 62A, and 64A, substantially conform to the curvature of the outer surface 18 of the acetabular cup 12. Additionally, the acetabular spacer members 60, 62, and 64 may include an area defining a substantially curved and raised appendage or ridge 66, 68, and 70 formed on the lower surface 60A, 62A, and 64A, respectively, thereof for mating, and more preferably, sliding engagement with the groove 20. Finally, each acetabular spacer member 60, 62, and 64 preferably has at least one throughbore 72. The throughbores 72 preferably include a threaded surface 74 thereon. It should be noted that the raised ridges 66, 68, and 70 are bisected by the respective throughbore 72.

The purpose of the raised ridges 66, 68, and 70, respectively, is to allow the respective acetabular spacer member 60, 62, or 64 to slidingly mate with the groove 20 on the outer surface 18 of the acetabular cup 12. This allows the surgeon the option of positioning the respective acetabular spacer member 60, 62, or 64 practically anywhere along the length of the groove 20 to best deal with the particular acetabular defect in the superior-posterior region. For example, the acetabular spacer member 60, 62, or 64 can slide in a superior-posterior direction with respect to the acetabulum. It is also envisioned that the acetabular spacer member 60, 62, or 64 can slide in a medial direction, as well. Once the final position of the acetabular spacer member is determined, the surgeon can then secure the respective acetabular spacer member to the acetabular cup 12 by inserting a fastening member, such as a surgical screw, through one or more available throughbores 72 which generally aligns with one or more of the throughbores 26 which bisect the groove 20. The screw may extend upwardly through the acetabular cup 12 and into the respective acetabular spacer member, with the screw tip not extending past the upper surface of the respective acetabular spacer member. The modified acetabular prosthesis 10 can then be installed in the acetabulum, as previously described, such that the acetabular spacer member 60, 62, or 64 is disposed between the outer surface 18 of the acetabular cup 12 and the acetabulum.

Unfortunately, the use of acetabular spacer members 60, 62, or 64 alone is sometimes not enough to address each and every particular clinical situation. The use of the acetabular spacer members 60, 62, or 64 may address the defect in the acetabulum, but it may not address a defect in the surrounding pelvic structures, or alternatively, the use of the acetabular spacer members 60, 62, or 64 may alter the attachment point of the attachment members 32, 34 or 36 such that an undesirable gap is created between the respective outer surfaces 32C, 34C, and 36C and the pelvis.

Therefore, the present invention employs at least one other augment or spacer member to compensate for the fact that the surrounding pelvic structures may have defects therein which prevent the outer surfaces 32C, 34C, and 36C of rigid attachment members 32, 34, and 36, respectively, from contacting the respective surfaces of the pelvis, i.e., the ischium and the ilium.

Figure 10:
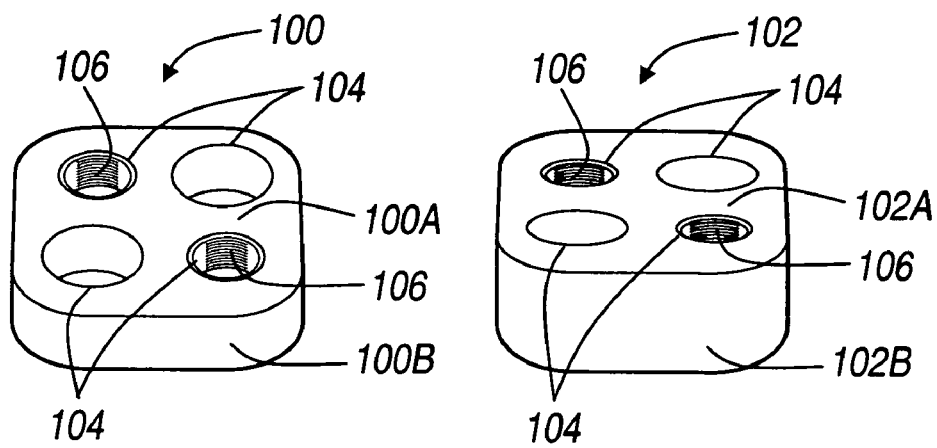
FIG. 10 is a front perspective view of two attachment spacer members for an acetabular prosthesis, in accordance with one embodiment of the present invention.
Figure 11:
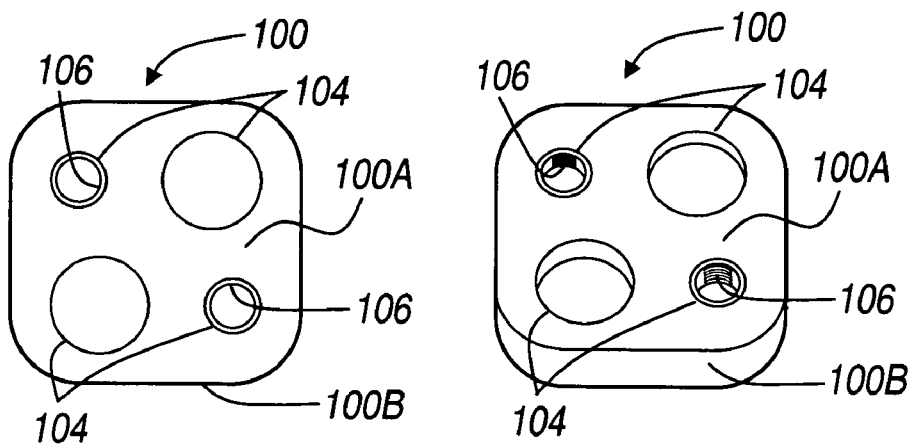
FIG. 11 is a top plan view of two attachment spacer members for an acetabular prosthesis, in accordance with one embodiment of the present invention.
Figure 12:
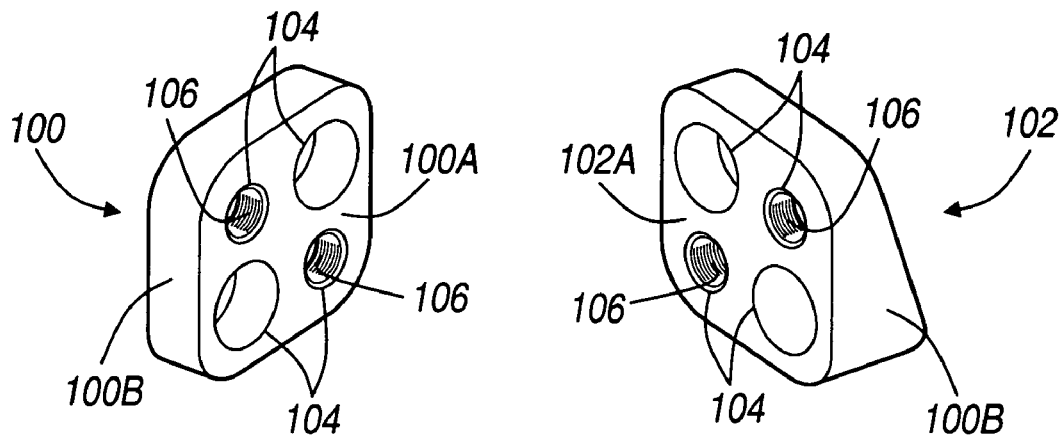
FIG. 12 is a side perspective view of two attachment spacer members for an acetabular prosthesis, in accordance with one embodiment of the present invention.

Referring to FIGS. 10-12, two different types of attachment spacer members 100 and 102 for use with the attachment members 32, 34, and 36, respectively, according to the general teachings of the present invention, are shown. It should be noted that more than one attachment spacer member can be used at one time in practice. For example, if there is a relatively small defect in the surface of the ischium, or attachment member 32 can not abut it, an attachment spacer member 100 or 102 can be employed. If there is a defect in the surface of the ilium (either anterior and/or posterior), or attachment member 34 or 36 can not abut it, an attachment spacer member 100 or 102 can be employed. It is envisioned that either smaller and/or larger attachment spacer members may also be employed with the present invention.

The attachment spacer members 100 and 102 generally have at least one flat surface 100A and 102A, respectively, for mating adjacently against the planar portions 32B, 34B, and 36B of attachment members 32, 34, and 36, respectively. The other surface of the attachment spacer members 100 and 102 may be either flat and parallel 100B or flat and non-parallel (i.e., inclined) 102B.

Each attachment spacer member 100 and 102 may have at least one throughbore 104. At least one of the throughbores 104 generally includes a threaded surface 106 thereon. The surgeon can then secure the respective attachment spacer member 100 or 102 to the outer surface 32C, 34C, or 36C, respectively, by inserting a fastening member, such as a surgical screw, through one or more available throughbores 104 which preferably aligns with one or more of the throughbores 40, 42, 44, respectively, in planar portions 32B, 34B, or 36B, respectively. The further modified acetabular prosthesis 10 then can be installed in the acetabulum, as previously described, such that the attachment spacer members 100 and/or 102 are disposed between the outer surface 32C, 34C, or 36C, respectively, of the planar portions 32B, 34B, or 36B, respectively, of the attachment members 32, 34, or 36, respectively, and the pelvis, i.e., the ischium and/or the ilium. Preferably, two diagonally opposed and spaced throughbores 104 are used to attach the attachment spacer member 100 and 102 to the outer surface 32C, 34C, or 36C, respectively, of the planar portions 32B, 34B, or 36B, respectively, of the attachment members 32, 34, or 36, respectively, and the pelvis, i.e., the ischium and/or the ilium. Bone screws (not shown) can then be inserted through the two diagonally opposed throughbores 104, and the aligned one or more of the throughbores 40, 42, 44, respectively, to secure the attachment members 32, 34, or 36, respectively, to the pelvis.

It should be noted that sometimes it is only necessary to use the attachment spacer members 100 and/or 102 alone, instead of using them in conjunction with an acetabular spacer member 60, 62, or 64. In that scenario, it is beneficial that the groove 20 is employed in the outer surface 18 of the acetabular cup 12, as opposed to a raised appendage or ridge which may interfere with the proper alignment of the acetabular cup 12, or might irritate the acetabulum.

Although the acetabular prosthesis 10, also referred to as a protrusio cage or protrusio acetabular prosthesis, may be implanted using any number of methods, the acetabular prosthesis 10 is generally implanted after employing a particular trialing prosthesis. The trialing acetabular prosthesis generally resembles the acetabular prosthesis 10, but may be constructed out of a less substantial material than the acetabular prosthesis 10. The trial acetabular prosthesis may also differ from the acetabular prosthesis 10 by not having a porous coat or as many throughbores. The trialing acetabular prosthesis allows the acetabular prosthesis to be placed in the acetabulum to assure a proper size and fit before attempting to secure the acetabular prosthesis 10 to the pelvic area. In addition, a trialing acetabular prosthesis allows the physician to determine the appropriate spacers, if necessary, or a slightly augmented orientation of the various attachment members 32, 34, and 36. Moreover, trial attachment members may be bent or deflected to determine if the attachment members 32, 34, and 36 should also be bent before implantation.

Figure 20:
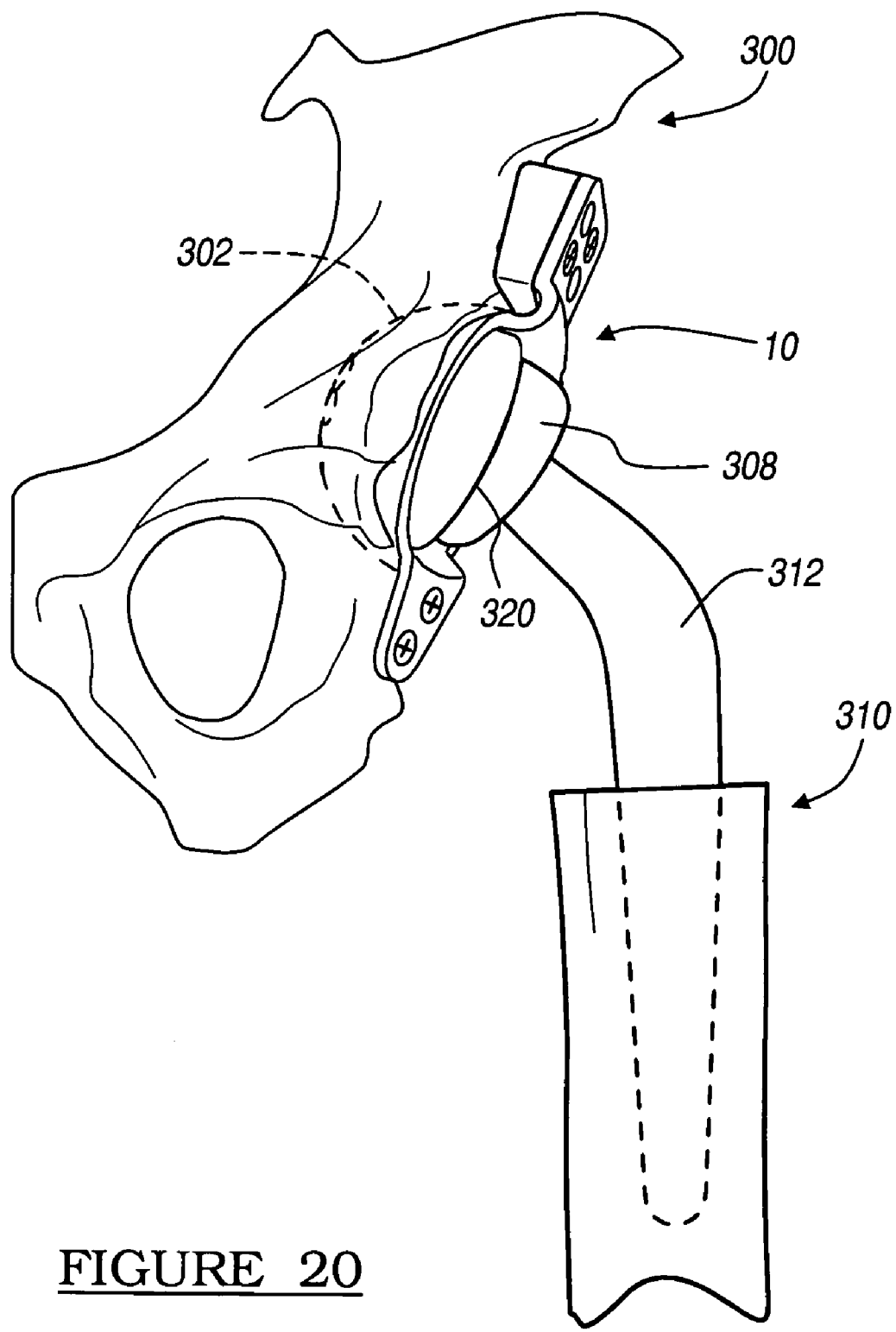
FIG. 20 is a perspective view of the protrusio cage and a cup being implanted after the trialing has occurred.
Figure 21:
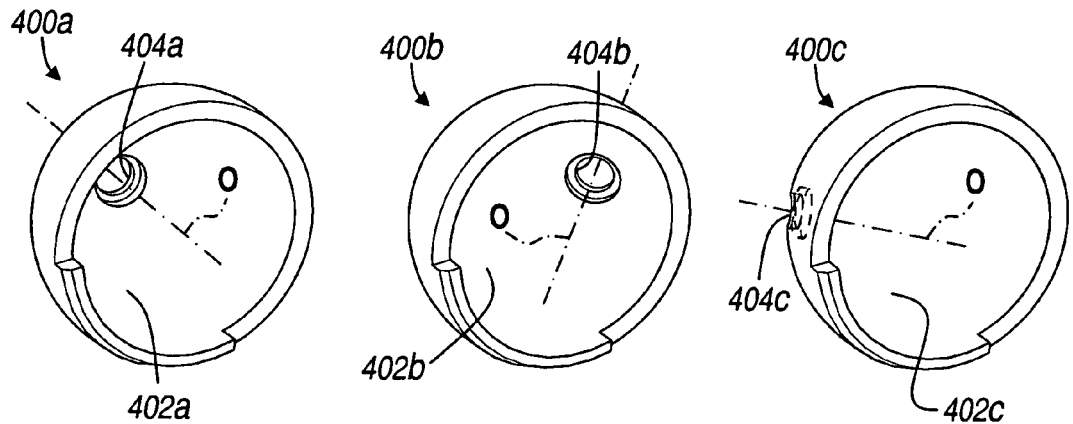
FIG. 21 is a perspective view of a series of trial shells according to an alternate embodiment.

Not only may a trialing component be provided for the acetabular prosthesis 10, but a trial shell or bearing liner 200 may also be provided. The trial shell 200 may be associated with the acetabular prosthesis 10 after it has been implanted to trial the appropriate position of the prosthetic shell (at 320 in FIG. 20) before implanting the prosthetic shell. The prosthetic shell, substantially resembles the trial shell 200, save that the prosthetic shell is substantially solid and continuous.

Figure 13:
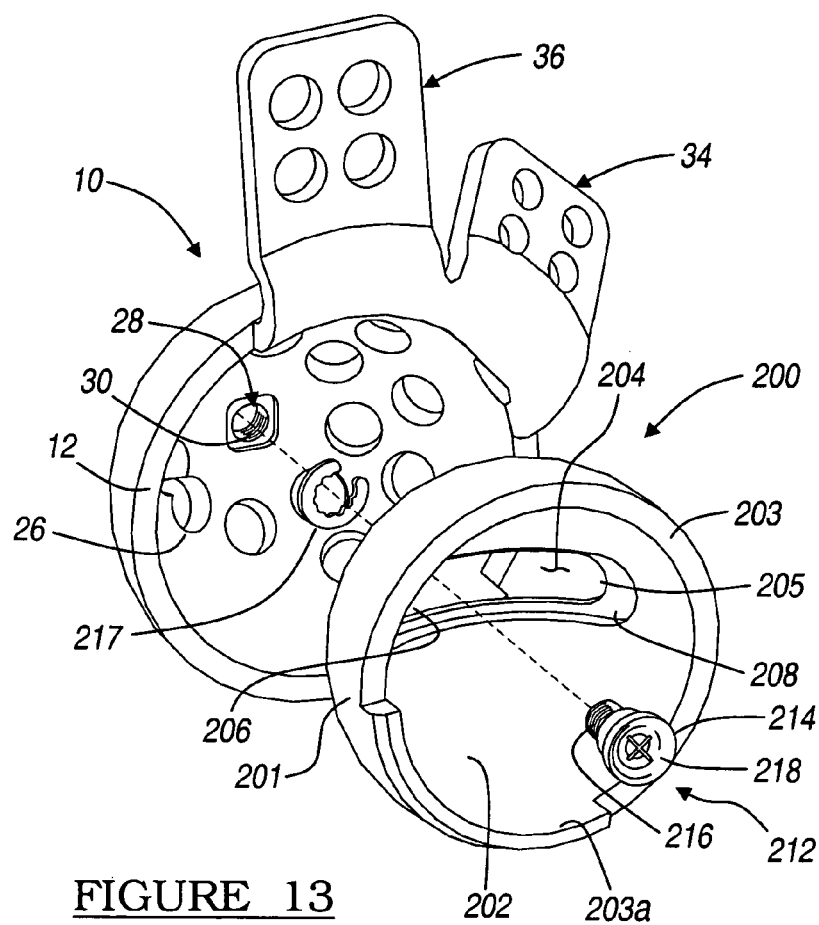
FIG. 13 is an exploded perspective view of a trialing cup and a protrusio cage.
Figure 14:
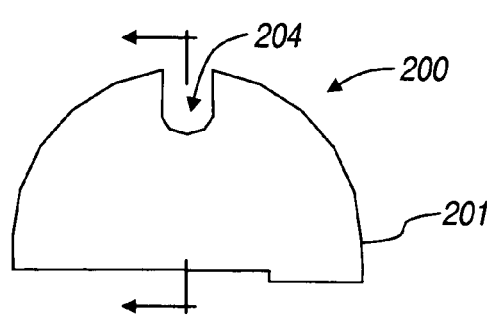
FIG. 14 is an elevational view of a trialing cup.
Figure 15:
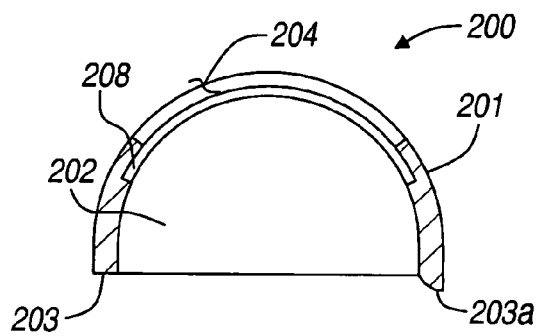
FIG. 15 is a cross-sectional view of a trialing cup.

With reference to FIGS. 13-15, the trial shell 200 generally include a shell that is substantially congruent to the acetabular cup 12 of the acetabular prosthesis 10. Thus, the trial shell includes an exterior 201 that is substantially convex that is substantially congruent with the acetabular cup 12. The trial shell 200 also includes an internal or shell recess 202, which is designed to substantially mate with either the ball of a femoral prosthetic or the head of a natural femur. Between the inner recess 202 and the exterior 201, and at a meridian of the trial shell 200, is a surface or wall 203. A raised ridge 203a may be provided on a portion of the wall 203.

Formed in and along an arc of the exterior 201 is a trial track or trial slot 204. The slot 204 passes substantially through the trial shell 200 and provides a passage from the exterior 201 to the internal recess 202. The slot 204 may reach substantially from a first side 205 to a second side 206 of the interior recess 202. The slot 204 provides a channel that reaches substantially across the trial shell 200. The slot 204 generally defines a total arc about 60° to about 120°. Therefore, the trial shell 200 may have a range of motion of about 60° to about 120°. It will be understood that various different trial shells may include an arc having a different angle. The slot 204 is an orientation portion of the trial shell 200, as described further herein. The slot 204 provides an area for a trial screw 212 to be received. Furthermore, a depression or countersink 208 substantially surrounds the perimeter of the slot 204.

The trial screw 212 would generally include a head portion 214 and a threaded shank 216. The head portion 214 may define a substantially arcuate top portion 218. The head portion 214 is substantially received or is nested in the countersink 208. After placing the screw 212 into the trial shell 200, the screw 212 would not interfere with a head or ball portion of a femur (illustrated in FIG. 19a-19c) since the head 214 rests within the countersink 208. The shank portion 216 is received through the slot 204 and may be held in place with a lock ring 217 or similar appropriate device. The trial shell 200, trial screw 212, and lock ring 217 form an assembly easily manipulated by a physician and eliminates a non-affixed component during the procedure. Once received through the slot 204, the threaded shank 216 may engage the threads 30 of the throughbore 28. The trial screw 212, when received through the slot 204 and tightened into the threads 30, would substantially not interfere with the inner recess 202. As mentioned above, the top portion 218 of the head 214 further defines the inner recess 202 or is substantially congruent therewith, such that when a head portion or ball portion of a hip prosthesis is inserted into the inner cup 202, the trial screw 212 does not interfere with movement of the head portion.

Figure 16:
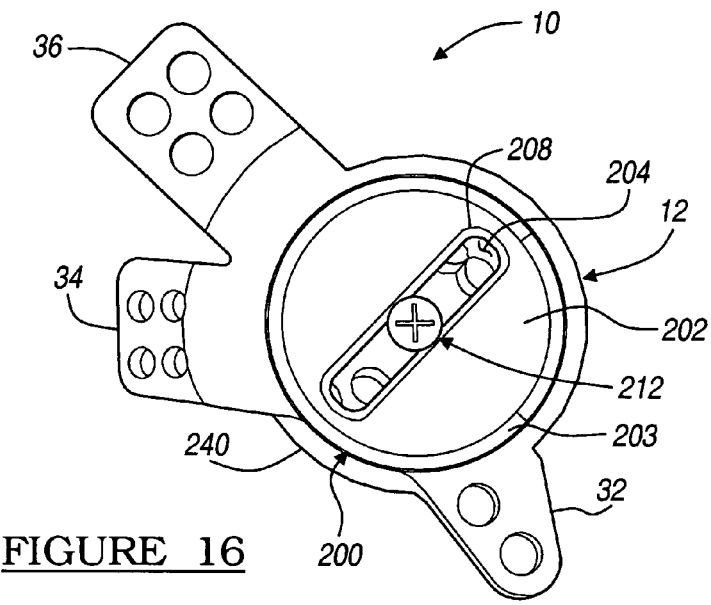
FIG. 16 is an elevated view of the trial cup held within a protrusio cage.

With reference to FIG. 16, once assembled, the trial shell 200 may be affixed substantially fixed and motionless relative the acetabular cup 12. This is accomplished by passing the trial screw 212 through the slot 204 of the trial shell 200 and engaging the threads 30 with the trial screw 212. The trial screw 212 may then be tightened against the recess 208, formed in the trial shell 200, to hold the trial shell 200 in a predetermined fastened position. In this position, the trial shell 200 is substantially immobile relative the acetabular cup 12. The trial screw 212 interacts with the threads 30 to provide an attachment or connection mechanism between the trial shell 200 and the acetabular cup 12. It will be understood, however, that other connection mechanisms may provide similar connections. For example a pin or removable rivet may be used to selectively fix the trial shell 200 in a selected orientation relative the acetabular cup 12.

The trial screw 212 may be loosened so that the trial shell 200 may be moved or adjusted defining a locating position and then reaffixed to the fastened position by tightening the screw 212 against the recess 208 of the trial shell 200. It will be understood that other appropriate shapes or types of screws may be used as the trial screw 212. Furthermore, any appropriate tool may be used to manipulate the trial screw 212.

Figures 17A, 17B:
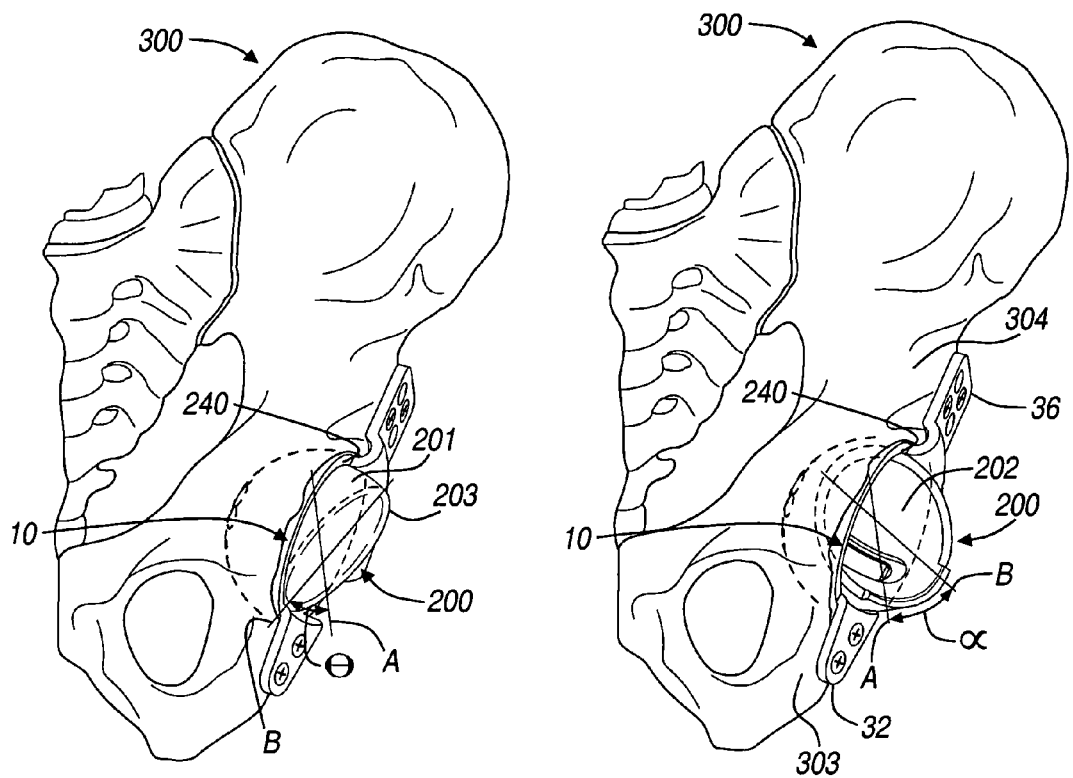

With reference to FIGS. 17a and 17b, the trial shell 200 may be positioned and fixed at a substantial plurality of orientations relative the acetabular prosthesis 10. For discussion purposes, the following axes are defined, nevertheless it will be understood that different references may provide different angles, but this will not alter the present discussion. A rim 240 of the acetabular cup 12 defines an acetabular cup plane A. The rim 203 of the trial shell 200 also defines a plane B. A third axis or axis of orientation C is defined by the shank 216 of the trial screw 212. It will be understood that the trial shell 200, when the trial screw 212 is loosened, may be moved along the slot 204 for its length and rotated substantially 360° around the trial screw 212. The various orientations of the trial shell 200 are relative the orientation axis C. The orientation axis C is also substantially defined by the throughbore 28 which is formed substantially at a pole of the acetabular cup 12.

One exemplary position will allow a negative angle $\theta$, specifically illustrated in FIG. 17a. The angles given are in reference to the relative orientation of the planes A and B when in a pelvis 300. Particularly, the relative orientation of the interior portion of the plane B relative to plane A. Therefore, when the angle $\theta$ is negative the trial shell plane B is below acetabular cup plane A. In this exemplary position, the trial screw 212 may be tightened to hold the trial shell 200 in place. With reference to FIG. 17b, a separate or different exemplary orientation may provide a positive angle $\alpha$. It will be understood that these are merely exemplary of the many plurality of orientations the trial shell 200 may have relative the acetabular prosthesis 10 by loosening the trial screw 212 and moving the trial shell 200 relative the acetabular prosthesis 10. This allows the trial shell 200 to be orientated for trialing of the femur before fixedly implanting the prosthetic shell into the acetabular cup 12 after implanting the acetabular prosthesis 10.

Figure 18:
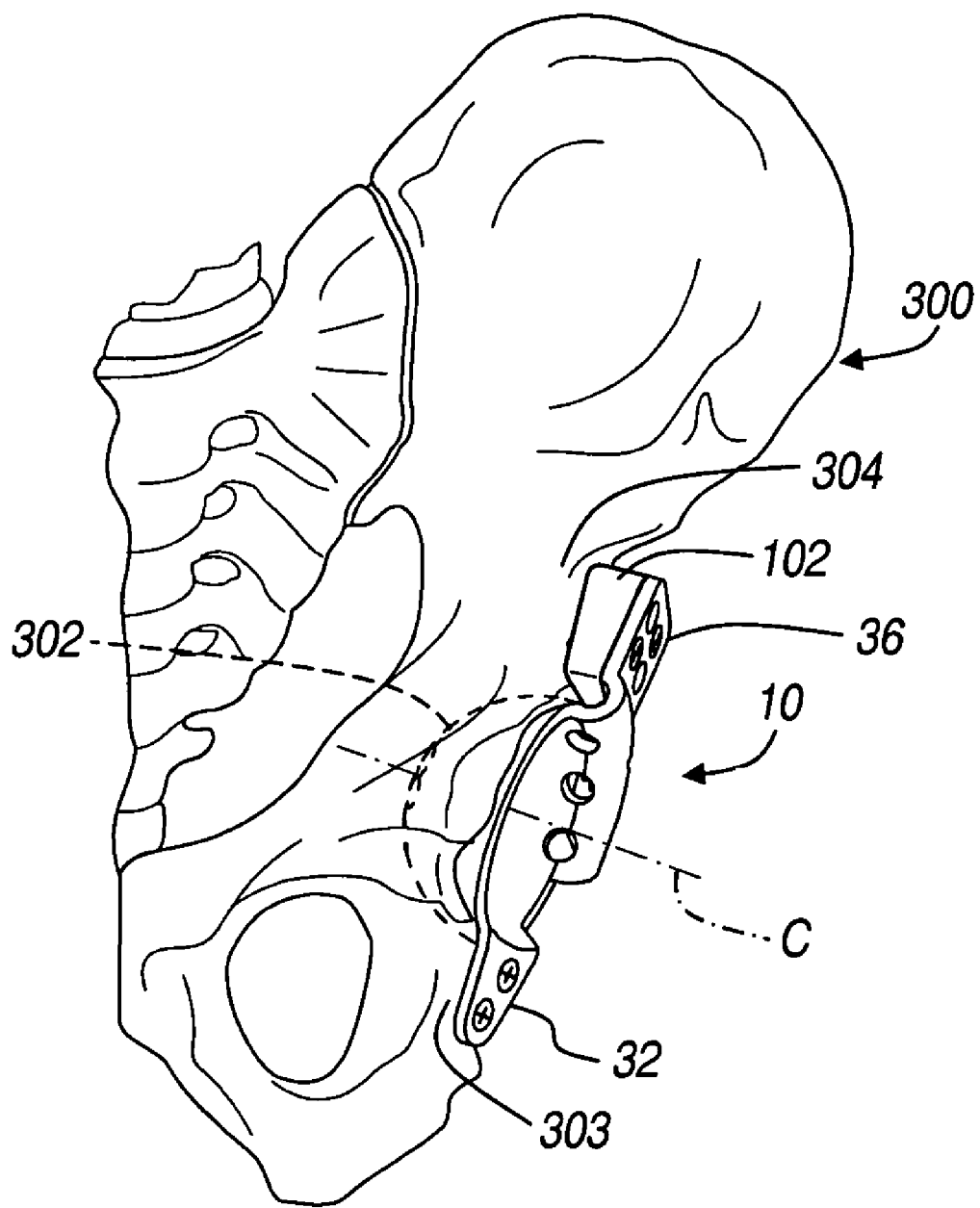
FIG. 18 is an elevational view of a protrusio cage and implanted in an acetabulum and a trialing cup held therein.

An exemplary method for using this system as disclosed herein, provides a method to both trial the acetabular prosthesis 10, with a trial acetabular prosthesis or protrusion cage, and to trial the trial shell 200 for the prosthetic liner 320. Initially, however, an acetabulum 302 is prepared as generally known in the art, and generally includes removing any extraneous cartilage, loose bone debris or other material that would interfere with the implantation of the acetabular prosthesis 10. After properly preparing the acetabulum 302, a trial acetabular prosthesis or trial protrusio cage can be trialed in the prepared acetabulum 302. As discussed above, the trial acetabular prosthesis is substantially similar to the acetabular prosthesis 10 save that it may have a smooth outside as opposed to a porous coat and other minor differences. The trial acetabular prosthesis will help the physician determine the proper implant size and placement of any necessary spacers or if any of the attachment members need to be repositioned, as by bending, before implanting the acetabular prosthesis 10. The physician may also determine a proper orientation using the trial acetabular prosthesis which is then mimicked when implanting the acetabular prosthesis 10. Once the physician has trialed the placement of the acetabular prosthesis 10, the appropriate spacers may be assembled and the proper orientation of the acetabular prosthesis 10 is easily determined. Then, the assembled components are implanted into the acetabulum 302 of the patient, including the acetabular prosthesis 10 in the appropriate orientation and the appropriate and necessary spacers, as illustrated in FIG. 18. The acetabular prosthesis 10 may be implanted using any appropriate methods such as using fastening members such as screws, or other fixation means such as bone cement. The attachment members 32, 34, and 36 are also affixed to the appropriate portions of the illium 303 and ischium 304 of the pelvis 300.

After the acetabular prosthesis 10 has been affixed in place, the trial shell 200 may be positioned in the acetabular cup 12 by placing the trial screw 212 through the slot 204 and engaging the threads 30 of the throughbore 28. Although the orientation axis C may be slightly different depending upon the individual into which the acetabular prosthesis 10 is implanted, the orientation axis C is generally does not lie on either the median plane or coronal plane of the patient. The trial shell 200 is oriented relative this orientation axis C by moving it along the slot 204 of the trial shell 200, as described above.

After the acetabular prosthesis 10 is implanted into the acetabulum, a first orientation of the trial shell 200 is chosen. The physician implanting the acetabular prosthesis 10 chooses a first orientation by placing the trial shell 200 at a desired orientation relative the acetabular cup 12 and fixing it in place by tightening the trial screw 212 against the recess 208 of the trial shell 200. After this occurs, the physician can determine whether an appropriate orientation has been chosen to allow range of movement for the hip joint. This is done by placing the head 308 of the femur 310 in place in the interior recess 202. The femur 310 is then moved through an appropriate range of motion to determine if the stem or neck 312 of the femur 310 engages any portion of the trial shell 200. It is generally desired to have a low or substantially no dislocation force when the femur 310 is moved through a general range of motion. If such a force were to occur the head 308 may dislocate from the inner recess 202. It will be understood that the head 308 may be a prosthetic head, a natural head, or a femoral replacement.

Figure 19A:
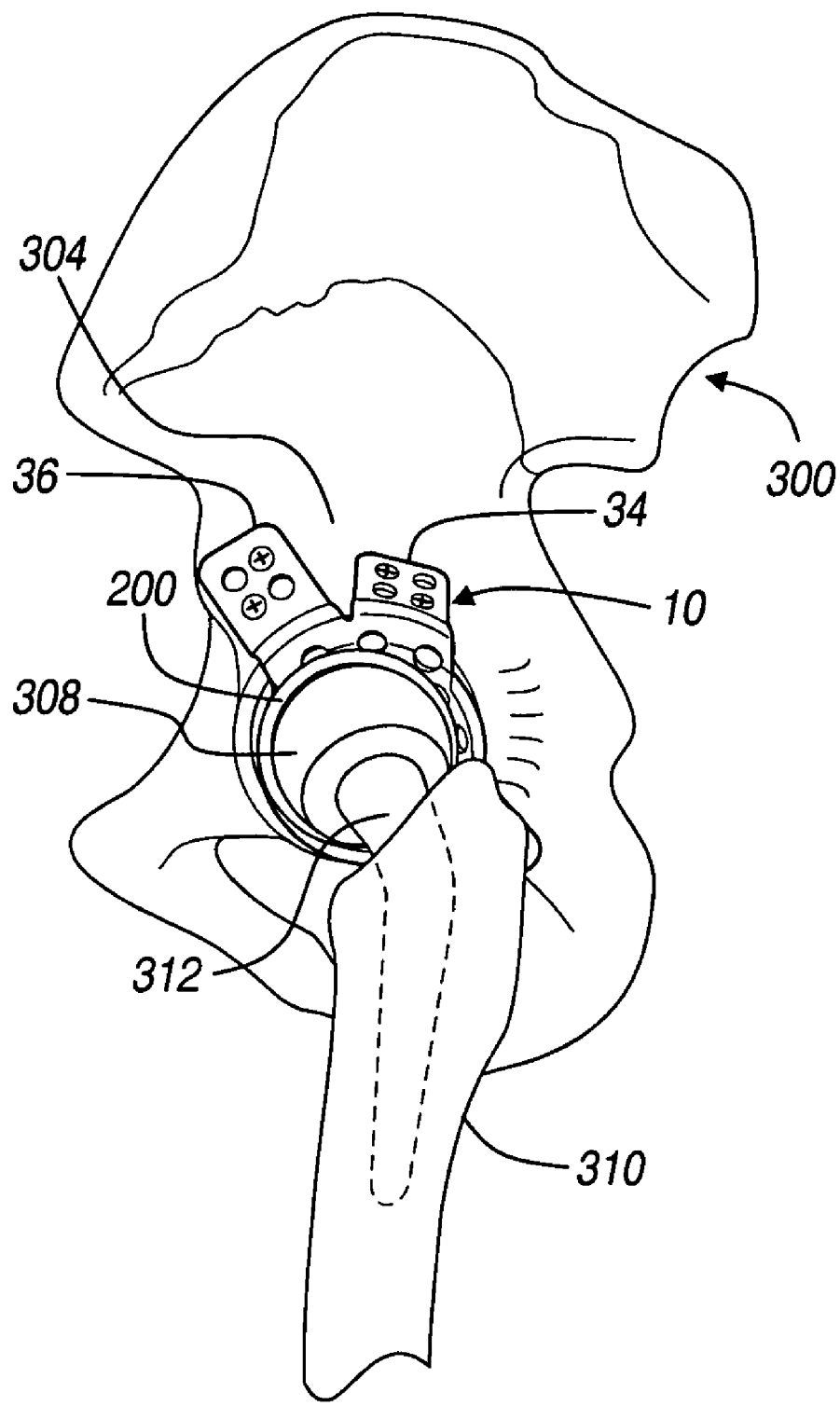
FIGS. 19A-19C illustrate a trial of the range of motion of a hip joint after the trialing cup has been affixed in a first trialing orientation.
Figure 19B:
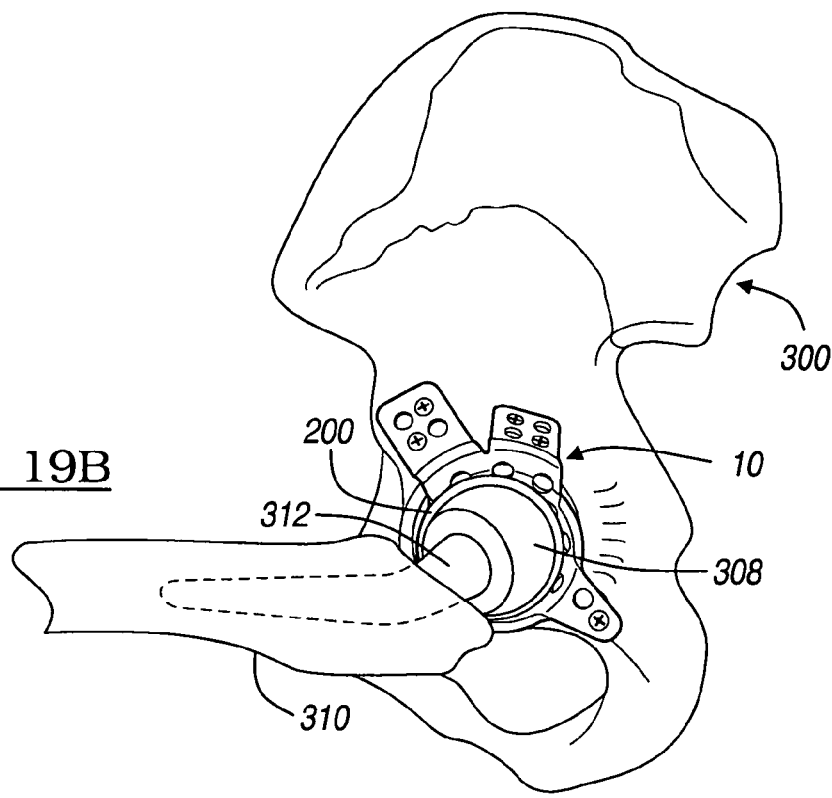
Figure 19C:
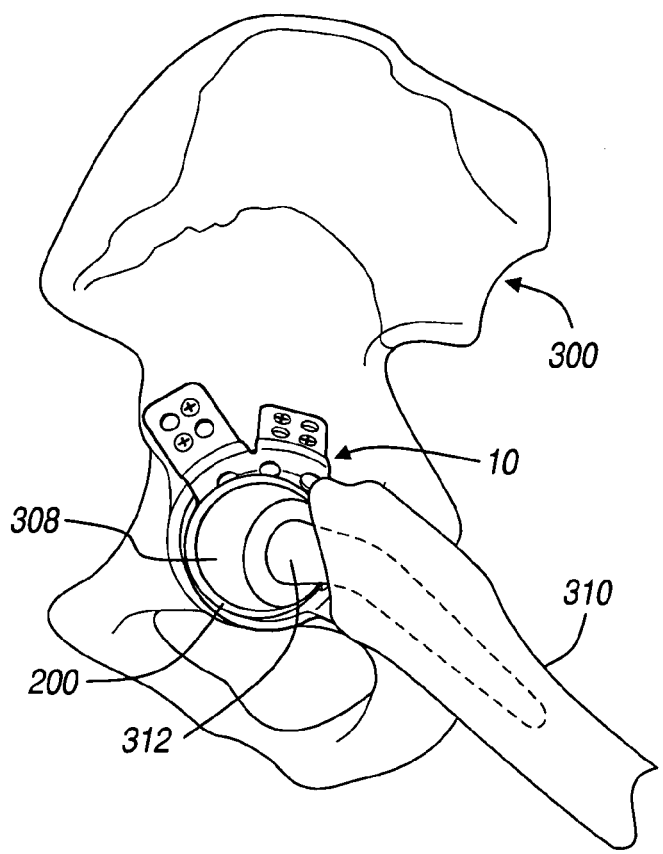

With reference to FIG. 19A, the femur 310 may first be moved to a natural or neutral position. With reference to FIG. 19B, the femur may then be moved to about 90° of flexion and taken through a range of internal rotation. And finally with reference to FIGS. 19C, the femur may be moved to about 30° of extension and taken through a range of external rotation. It will be understood the femur 310 is generally moved fluidly and continuously from position to position. Also, a plurality of other specific positions may be trialed. In any of these positions, a contact between the femur 310 and the trial shell 200 may be felt or seen by the physician. Furthermore, a dislocation of the head from the trial shell 200 would also be ascertained. If the physician determines that the neck 312 of the femur 310 or the femur itself engages or contact a portion of the trial shell 200; or if the head 308 dislocates from the inner recess 202, the physician may attempt a different position of the trial shell 200. The trial shell 200 may be moved by first loosening the trial screw 212 moving the trial shell 200 to a different orientation, exemplarily illustrated in FIG. 17a or 17b, and retightening the trial screw 212 to hold the trial shell 200 substantially fixed in the new position. The physician may then trial the hip joint by moving the femur 310 again through a range of motion to determine whether any portion of the femur 310 engages a portion of the trial shell 200 or if the head 308 dislocates from the trial shell 200.

When the physician determines the proper orientation has been selected, the physician may then note the orientation and position of the trial shell 200. This may be done through any appropriate method, such as marking the orientation on the trial shell 200 or noting the orientation of the trial shell 200. The trial shell 200 may also include demarcations on the exterior 201. These demarcations may be noted when the orientation of the trial shell 200 is selected. Similar demarcations may be included on the exterior of the prosthetic shell 320 and may be used to match the orientation of the prosthetic shell 320 to the selected orientation. Alternatively the demarcations may provide a reference for placing the prosthetic shell 320.

Therefore, after the appropriate orientation is selected, the femur 310 is again dislocated from the inner recess 202 and the trial screw 212 and trial shell 200 are removed from the acetabular prosthesis 10. This is performed by simply removing the trial screw 212 and then removing the trial shell 200 from the acetabular prosthesis 10. After this occurs, a prosthetic shell or liner 320 may be implanted into the acetabular prosthesis 10. The prosthetic shell 320 is placed into the acetabular prosthesis 10 according to the determined orientation of the trial shell 200. It will be understood, therefore, that the trial shell 200 and the prosthetic shell 320 generally are similar in size and shape. Although the trial shell 200 may differ if the differences are accounted for in the procedure, such as offset or roundness of the trial shell 200 compared to the prosthetic liner 320. The prosthetic shell 320 is then permanently affixed in place using an appropriate means, such as a bone cement. The bone cement substantially permanently affixes the prosthetic shell 320 in place, such that after the femur 310 is placed to engage the prosthetic shell 320, the shell 320 does not move.

Therefore, a proper orientation of the shell 320 may be determined before the shell 320 is implanted into the acetabular prosthesis 10. The trial shell 200 allows a selection of a proper orientation of the shell 320 using a removably fixation means, such as the trial screw 212. This allows the physician to trial several orientations of the trial shell 200 before permanently affixing, or substantially permanently affixing a shell 320 into the acetabular prosthesis. Therefore, the appropriate orientation of the shell can be determined more precisely and with substantially little error by using the trial shell 200.

Turning now to FIGS. 21-25, the present invention according to an alternate embodiment incorporating a series of trial shells 400a-400c will be described. In this embodiment, the series of trial shells 400a-400c are used in place of the trial shell 200. Each trial shell 400a-400c includes an inner surface 402a-402c having an attachment device or passage 404a-404c thereon for accepting the trial screw 212. Each attachment passage 404a-404c of each trial shell 400a-400c is located at a unique location on the surface 402a-402c thereof. As will be described in greater detail, the unique placement of each attachment passage 404a-404c allows a selected trial shell 400a-400c to be located at a distinct angle with respect to the acetabular prosthesis 10 in a fastened position. Each trial shell 400a-400c is movable in one degree of freedom about an orientation axis O defined by the attachment passage 404a-404c.

Figure 22:
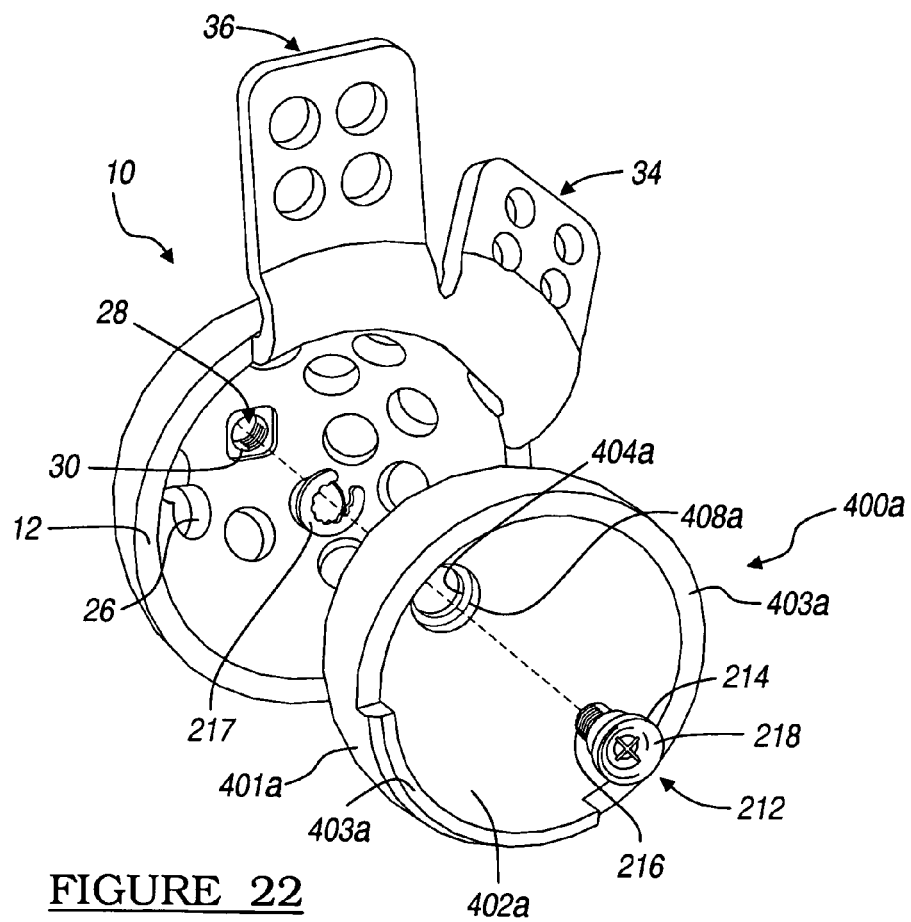
FIG. 22 is an exploded perspective view of one of the trial shells and a protrusio cage.

With specific reference to FIG. 22, the trial shell 400a generally includes a shell that is substantially congruent to the acetablular cup 12 of the acetabular prosthesis 10. As shown, the features of trial shell 400a are designated with similar reference numerals from those associated with trial shell 200 and include a 400 prefix. The trial shell 400a includes an exterior 401a that is substantially convex and congruent with the acetabular cup 12. The trial shell 400a also includes an internal or shell recess 402a designed to substantially mate with either the ball of a femoral prosthetic or the head of a natural femur. Between the inner recess 402a and the exterior 401a, and at a meridian of the trial shell 400a, is a surface or wall 403a. A raised ridge 403a may be provided on a portion of the wall 403a. Passage 404a is further defined by a countersink 408a for receiving the head portion 214 in a fastened position. Accordingly, after placing the screw 212 into the trial shell 400a, the screw 212 will not interfere with a head or ball portion of the femur.

Figure 23:
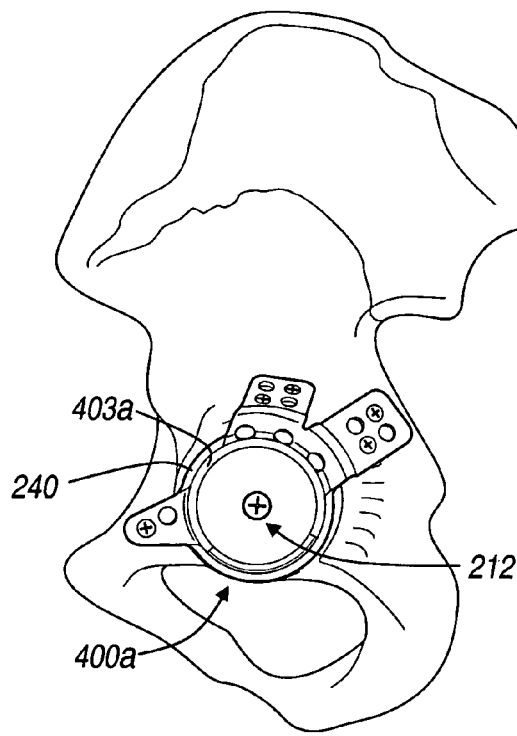
FIG. 23 is an elevated view of the trial cup of FIG. 22 held within a protrusio cage.

With reference to FIG. 23, the trial shell 400a is shown in a fastened position with the acetabular cup 12. The location of passage 404a on the surface 402a of the trial cup 400a is generally centralized or, more specifically, the orientation axis O extends through a centerpoint of a radius defined by the wall 403 of the trial shell 404a. As a result, the wall 403a of the trial shell 400a is substantially flush to the rim 240 of the acetabular cup 12 in a fastened position. In the locating position, the acetabular cup 400a is moveable in one degree of freedom about the trial screw 212 and the orientation axis O.

Figure 24:
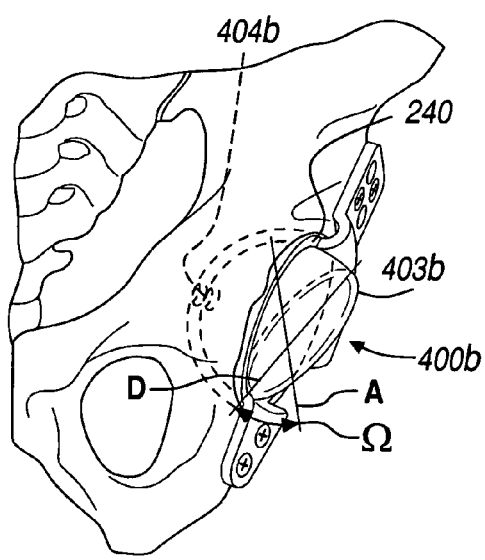
FIG. 24 is a perspective view of a protrusio cage implanted in an acetabulum and a first trialing cup in a first position.
Figure 25:
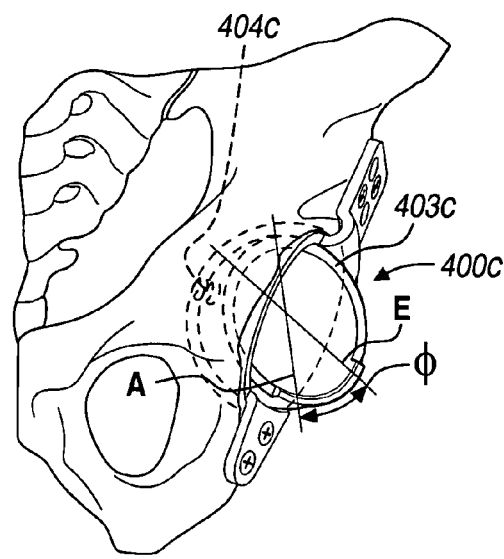
FIG. 25 is a protrusio cage implanted in an acetabulum and a second trialing cup in a second position different from that illustrated in FIG. 24.

Referring now to FIGS. 24 and 25 the trial shells 400b and 400c will be described in a fastened position. The trial shell 400b is shown received by the acetablular cup 12 in FIG. 24. A rim 403b of the trial shell 400b defines a plane D. As shown, the trial shell 400b is positioned at a negative orientation angle Ω defined between the respective planes A and D. Again, the trial shell 400b is rotatable in one degree of freedom about the trial screw (not specifically shown).

In FIG. 25, the trial shell 400c is shown received by the acetabular cup 12. A rim 403c of the trial shell 400c defines a plane E. The trial shell 400c is positioned at a positive orientation angle φ defined between the respective planes A and E. The trial shell 400c is rotatable in one degree of freedom about the trial screw. It is appreciated that alternative attachment passage locations may be provided on the trial shells 400a-400c. In addition, an alternate amount of trial shells may be provided for achieving a desired plurality of distinct orientation angles.

An exemplary method for using the collection of trial shells 400a-440c will now be described. After the acetabular prosthesis 10 has been affixed to the patient, a first trial shell 400a may be positioned in the acetabular cup 12 by placing the trial screw 212 through the attachment passage 404a. The trial screw 212 is subsequently tightened to engage the threads 30 of the throughbore 28 in the locating position. If desired, the physician may rotate the trial shell 400a 360 degrees about the orientation axis O to a predetermined location. The trial screw 212 is then tightened into the fastened position.

After this occurs, the physician determines if the proper angle is presented between the acetabular cup rim 240 and the trial cup rim 403a. This is accomplished by placing the head 308 of the femur 310 into the interior recess 402. The femur 310 is then moved through an appropriate range of motion to determine if the stem or neck 312 of the femur 310 engages any portion of the trial shell 400a. Additionally, it is determined if the head 308 dislocates from the trial shell 400a. If it is determined that the neck 312 of the femur 310 is contacting the trial shell 400a or the head 308 is dislocates from the trial shell 400a, the trial screw 212 is removed and the trial shell 400a is replaced by another trial shell 400b, 400c. The process is repeated until a selected trial shell 400 provides a favorable orientation angle that eliminates contact of any portion of the trial shell 400 with the neck 312 of a rotating femur 310 and precludes the head 308 from dislocating from the trial shell 400.

Finally, demarcations are noted on the trial cup 400 as described with respect to the trial cup 200. The demarcations are similarly included on the exterior or the prosthetic shell 320 and are used to match the orientation of the prosthetic shell 320 to the selected orientation. Thereafter, the femur 310 is dislocated from the inner recess 402 and the trial shell 400 is removed from the acetabular prosthesis 10. The prosthetic shell 320 is then placed into the acetabular prosthesis 10 according to the determined orientation of the trial shell 400.

Figure 26:
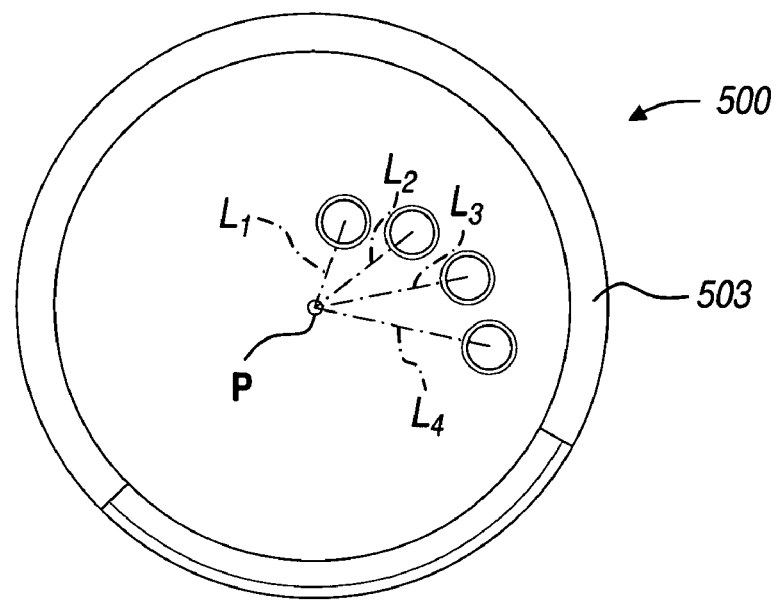
FIG. 26 is an elevated view of a trial cup according to a third embodiment.
Figure 27:
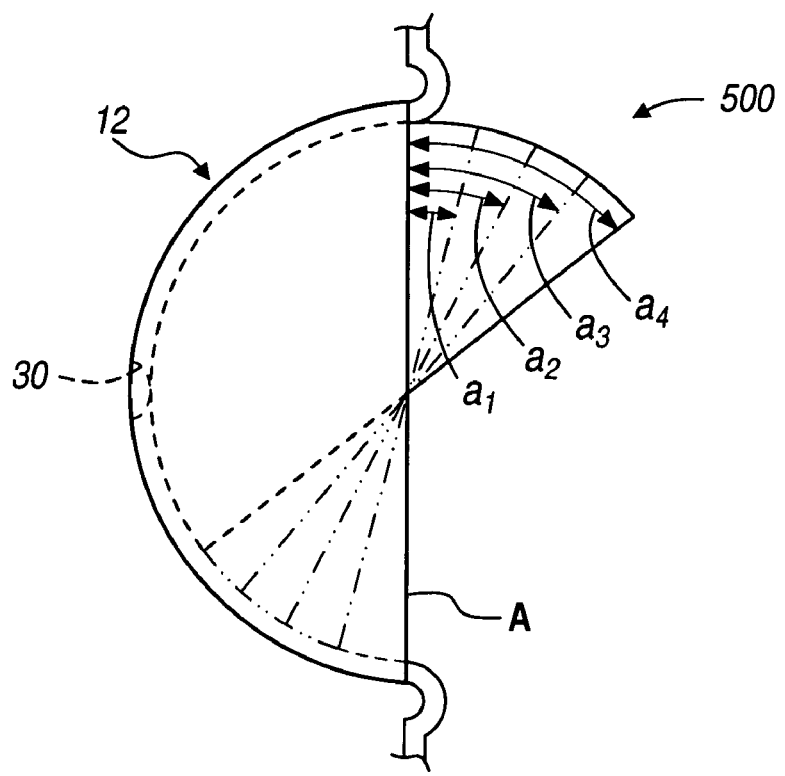
FIG. 27 is a side view of the trial cup of FIG. 26 illustrating a range of available orientation angles.

With reference to FIGS. 26 and 27, a trial shell 500 according to an alternate embodiment is shown having a plurality of passages 504a-504d incorporated thereon. The trial shell 500 provides a single shell having a plurality of mounting points yielding a plurality of angles ($a_1$-$a_4$) with respect to the plane A of the acetabular cup 12. Each passage 504a-504d is located a circumferential distance ($L_1$-$L_4$) from a point P intersecting the centerpoint of the radius defined by wall 503 of the trial shell 500. Again, while in the locating position, the acetabular cup 500 is moveable in one degree of freedom about the trial screw 212 in each passage 504a-504d. The angles $a_1$-$a_4$ preferably range from 0 to 40 degrees, however, alternate angles may similarly be provided.

The description of the invention is merely exemplary in nature and, thus, variations that do not depart from the gist of the invention are intended to be within the scope of the invention. Such variations are not to be regarded as a departure from the spirit and scope of the invention.

What is claimed is:
1. A system to provide a determination of an alignment of a prosthetic bearing, the system comprising:
   an acetabular prosthesis having a threaded receiving bore;
   a trial bearing liner;
   a plurality of attachment passages defined by the trial bearing liner each attachment passage located at a different position from an apex of said trial bearing liner; and
   an attachment member having a length to pass through any one of the attachment passages and interconnect the acetabular prosthesis at said threaded receiving bore and the trial bearing liner;
   wherein the attachment member is moveable between a locating position and a fastened position to selectively interconnect said trial bearing liner to the acetabular prosthesis via any one of said plurality of attachment passages;

wherein said trial bearing liner is only moveable to rotate around an axis defined by said attachment member in said locating position and substantially immobile relative to the acetabular prosthesis in said fastened position.

2. The system of claim 1, wherein the acetabular prosthesis includes:
an acetabular cup generally defining a portion of a hollow sphere and defining the threaded receiving bore, said attachment member engaging said acetabular cup at said the threaded receiving bore in said locating position and said fastened position.

3. The system of claim 2 wherein said attachment member includes:
an attachment end engaged with said the threaded receiving bore;
a central portion extending through at least one of said plurality of attachment passages; and
an engagement end operable to move said attachment member between said locating position and said fastened position.

4. The system of claim 1 wherein the acetabular cup includes an outer rim defining an acetabular cup plane and said trial bearing liner includes an outer rim defining a trial bearing liner plane, wherein the location of at least one of said plurality of attachment passages determines a predetermined angle said trial bearing liner plane is oriented relative to the acetabular cup plane.

5. The system of claim 4 wherein said predetermined angle is between 0 and 40 degrees.

6. A system to provide a determination of an alignment of a prosthetic bearing in an acetabular prosthesis, the system comprising:
a trial bearing liner or trial shell defining an attachment passage that extends between and through both an inner recess surface and an outer convex surface, the inner recess surface further has a countersink around the attachment passage;
an attachment member moveable between a locating position and a fastened position to selectively and operably interconnect said trial bearing liner or trial shell to the acetabular prosthesis via passing through said attachment passage, said attachment member includes:
an attachment end engagable with a bore defined by the acetabular prosthesis;
a central portion extending through said attachment passage; and
a head portion for manipulating said attachment member between said locating position and said fastened position and wherein the head portion is received in said countersink in said fastened position; and
a lock ring to affix said attachment member to said trial bearing liner or trial shell while the trial bearing liner or the trial shell is moved and prior to the attachment member moving to the locating position or the fastened position;
wherein said trial bearing liner or trial shell is only moveable to rotate around an axis defined by said attachment member in said locating position and substantially immobile relative to the acetabular prosthesis in said fastened position.

7. The system of claim 6 wherein the trial bearing liner defines a plurality of trial bearing liner attachment passages therethrough and each of said plurality of trial bearing liner attachment passages is offset a different distance from an apex of the trial bearing liner and the trial shell defines a plurality of trial shell attachment passages therethrough and each of said plurality of trial shell attachment passages is offset a different distance from an apex of the trial shell.

8. A system to provide a determination of an alignment of a prosthetic bearing in an acetabular prosthesis, the system comprising:
a first trial bearing liner having a first upper rim that defines a first trial bearing liner plane and defining a first attachment passage extending through the first trial bearing liner;
a second trial bearing liner having a second upper rim that defines a second trial bearing liner plane and defining a second attachment passage extending through the second trial bearing liner; and
an attachment member alternatively extendable through each of the first attachment passage or the second attachment passage and moveable between a locating position and a fastened position;
wherein the attachment member alternatively interconnects one of said first and second trial bearing liner to the acetabular prosthesis via said respective attachment passage;
wherein each of said first and second trial bearing liner rotates around an axis defined by said attachment member when said attachment member is in said locating position;
wherein said first trial bearing liner plane is oriented at a first angle relative to an acetabular cup plane defined by an acetabular cup upper rim in said locating position and said second trial bearing liner plane is oriented at a second angle relative to said acetabular cup plane in said locating position;
wherein said second angle is different from said first angle.

9. The system of claim 8 wherein said first attachment passage is defined at a first location on a dome of said first trial bearing liner from said second attachment passage defined at a different second location on a dome on said second trial bearing liner.

10. The system of claim 8, wherein the acetabular prosthesis includes:
an acetabular cup generally defining a portion of a hollow sphere and defining a bore, said attachment member engaging said bore in said locating position and said fastened position.

11. The system of claim 8, wherein said attachment member includes:
an attachment end operable to engage said acetabular cup via said bore
a central portion extending through said attachment passage; and
an engagement end for manipulating said attachment member between said locating and said fastened position.

12. The system of claim 8, further comprising a third trial bearing liner defining a third trial bearing liner plane and defining a third attachment passage, said third trial bearing liner plane defining a third distinct angle relative to said acetabular cup plane from said first and second trial bearing liner plane when assembled in said locating position.

13. The system of claim 12 wherein said first, second and third angle is between 0 and 40 degrees.

14. The system of claim 8 wherein said first or second attachment passages allow said attachment member to pass through said first or second trial bearing liner.

15. A system to provide a determination of an alignment of a prosthetic bearing in an acetabular prosthesis, the system comprising:

a first trial bearing liner defining a first attachment throughbore at a first position offset a first distance from a first apex of the first trial bearing liner;

a second trial bearing liner defining a second attachment throughbore at a second position offset a second distance different from the first distance from a second apex of the second trial bearing liner;

an attachment member moveable between a locating position and a fastened position to selectively and alternatively interconnect each of said first and second trial bearing liner to the acetabular prosthesis through said respective attachment throughbore, each of said first and second trial bearing liner moveable to only rotate around an axis defined by said attachment member in said locating position; and a locking member adapted to engage said attachment member to operably couple said attachment member and one of said first and second trial bearing liner;

wherein the first attachment throughbore of the first trial bearing liner and the second attachment throughbore of the second trial bearing liner are operable to allow the first trial bearing liner and the second trial bearing liner to be positioned at different angles relative to the acetabular prosthesis with the locking member.

16. A system to provide a determination of an alignment of a prosthetic, the system comprising:

an acetabular prosthesis operable to be implanted;

a trial bearing liner defining an attachment passage;

an attachment member moveable between a locating position and a fastened position to selectively and operably interconnect said trial bearing liner to said acetabular prosthesis via said attachment passage; and said acetabular prosthesis having an acetabular cup defining a portion of a hollow sphere and defining a threaded bore surrounded by a depression, said attachment member engaging said acetabular cup via said bore in said locating position and said fastened position;

wherein said attachment member passes through and engages said attachment passage in said trial bearing liner and said threaded bore in said acetabular cup;

wherein said trial bearing liner is moveable to only rotate around an axis defined by said attachment member in said locating position and substantially immobile relative to said acetabular prosthesis in said fastened position.

17. The system of claim 16 wherein said attachment member includes:

an attachment end engaged with said acetabular cup via said threaded bore;

a central portion extending through said attachment passage; and an engagement end operable to move said attachment member between said locating position and said fastened position.

18. The system of claim 16 wherein the acetabular cup includes an outer rim defining an acetabular cup plane and said trial bearing liner includes an outer rim defining a trial bearing liner plane, wherein the location of said attachment passage determines a predetermined angle said trial bearing liner plane is oriented from the acetabular cup plane.

19. The system of claim 18 wherein said predetermined angle is between 0 and 40 degrees.

20. The system of claim 16, wherein the trial bearing liner defines a plurality of the attachment passages each at different positions from an apex of the trial bearing liner;

wherein when interconnected with the acetabular cup allow a trial liner plane defined by the trial bearing liner to be positioned at a different angle relative to an acetabular cup plane defined by the acetabular cup.

21. A system to provide a determination of an alignment of a prosthetic, the system comprising:

an acetabular prosthesis having a threaded bore formed in a wall of the acetabular prosthesis;

a trial bearing liner defining an attachment throughbore;

an attachment member moveable between a locating position and a fastened position to selectively and operably interconnect said trial bearing liner to said acetabular prosthesis via said attachment throughbore; and a lock ring adapted to engage said attachment member to operably couple said attachment member and said trial bearing liner prior to engaging the threaded bore;

wherein said trial bearing liner is moveable in one degree of freedom around an axis defined by said attachment member in said locating position and substantially immobile relative to said acetabular prosthesis in said fastened position;

wherein said attachment member includes:

an attachment end engagable with the threaded bore formed in said acetabular prosthesis;

a central portion extending through said attachment throughbore; and an engagement end operable to move said attachment member between said locating and said fastened position.

22. A method of implanting an acetabular prosthesis in an acetabulum and providing a liner in the acetabular prosthesis in a selected orientation, the method comprising:

implanting the acetabular prosthesis having an acetabular rim defining an acetabular plane and a throughbore defining a throughbore axis;

selecting a first trial bearing liner wherein said first trial bearing liner has an upper rim defining a first trial liner plane having first angle relative to a first axis defined by a first attachment passage extending through said first trial bearing liner, wherein the attachment passage is offset from an apex of the first trial bearing liner;

disposing said first trial bearing liner in said implanted acetabular prosthesis to form a first trialing angle between said acetabular plane and said first trial liner plane;

rotating said first trial bearing liner around said throughbore axis to form a plurality of trialing orientations between said acetabular plane and said first trial liner plane;

fixing said first trial bearing liner at one of said trialing orientations with an attachment member that selectively couples said first trial bearing liner to the acetabular prosthesis;

locking the attachment member to said first trial bearing liner; and moving a femur through a range of motion relative to the first trial bearing liner after fixing said first trial bearing liner at one of said trialing orientations.

23. The method of claim 22 further comprising:

removing said first trial bearing liner;

disposing a second trial bearing liner in said acetabular prosthesis, said second trial bearing liner having an upper rim defining a second plane and extending at a second angle from said acetabular prosthesis, said second angle being distinct from said first angle;

rotating said second trial bearing liner to form a plurality of a second trialing orientations;

fixing said second trial bearing liner in one of said plurality of second trialing orientations; and moving said femur through a range of motion relative to said second trial bearing liner.

24. The method of claim 22 wherein fixing the first trial bearing liner includes actuating said attachment member into a fastened position wherein said first trial bearing liner is substantially immobile relative to the acetabular prosthesis.

25. The method of claim 22, further comprising:
placing a head extending from said femur in said first trial bearing liner; and
determining the presence of contact between said femur and said first trial bearing liner.

26. The method of claim 22, further comprising:
passing the attachment member through a second attachment passage to connect the first trial bearing liner and the implanted acetabular prosthesis;
wherein the second attachment passage allows the first trial bearing liner to rotate around a second attachment passage axis different than a first attachment passage axis and define a second angle of the first trial liner plane relative to the acetabular plane.

27. A method of implanting an acetabular prosthesis in an acetabulum and providing a liner in the acetabular prosthesis in a selected orientation, the method comprising:
implanting the acetabular prosthesis, the acetabular prosthesis having a rim that defines an acetabular cup plane;
disposing a first trial bearing liner in said implanted acetabular prosthesis;
rotating said first trial bearing liner around a first attachment passage axis to select a first orientation of the trial bearing liner relative to the acetabular cup plane defined by the acetabular prosthesis;
fixing said first trial bearing liner in said first orientation;
determining the presence of contact between a femur and said first trial bearing liner; and
removing said first trial bearing liner from the implanted acetabular prosthesis and placing a second trial bearing liner in said implanted acetabular prosthesis based on said determination of a presence of contact, wherein said second trial bearing liner is operable to be rotated to a second orientation relative to the acetabular prosthesis.

28. The method of claim 27 wherein determining the presence of contact includes:
placing a head extending from said femur in said first trial bearing liner;
moving said femur through a range of motion while maintaining said head in said first trial bearing liner.

29. The method of claim 27 wherein disposing a first trial bearing liner includes:
placing said first trial bearing liner in the acetabular prosthesis;
aligning a first attachment passage defined by said first trial bearing liner with a bore defined by the acetabular prosthesis; and
engaging the acetabular prosthesis with an attachment member at said bore and through a first attachment passage that is offset from an apex of the first trial bearing liner and that defines the first attachment passage axis, thereby coupling said first trial bearing liner with the acetabular prosthesis.

30. The method of claim 29 wherein fixing said first trial bearing liner includes actuating said attachment member into a fastened position wherein said first trial bearing liner is substantially immobile relative to the acetabular prosthesis.

31. The method of claim 29 wherein replacing said first trial bearing liner includes:
removing said attachment member from engagement with said first trial bearing liner and the acetabular prosthesis;
removing said first trial bearing liner from the acetabular prosthesis;
placing said second trial bearing liner in the acetabular prosthesis;
aligning a second attachment passage defined by said second trial bearing liner with said bore; and
engaging the acetabular prosthesis with said attachment member at said bore through a second attachment passage defining the second attachment passage axis thereby coupling said second trial bearing liner with the acetabular prosthesis.

* * * * *